(12) United States Patent
Kim et al.

(10) Patent No.: US 10,420,533 B2
(45) Date of Patent: Sep. 24, 2019

(54) ULTRASOUND DIAGNOSIS APPARATUS AND CONTROL METHOD THEREOF

(71) Applicant: Samsung Electronics Co., Ltd., Suwon-si, Gyeonggi-do (KR)

(72) Inventors: Yun-Kyung Kim, Suwon-si (KR); Hyun-Jin Kim, Seoul (KR); Mi-Young Lee, Seoul (KR); Su-yeon Jung, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 908 days.

(21) Appl. No.: 14/931,105

(22) Filed: Nov. 3, 2015

(65) Prior Publication Data

US 2016/0120508 A1 May 5, 2016

Related U.S. Application Data

(60) Provisional application No. 62/074,834, filed on Nov. 4, 2014.

(30) Foreign Application Priority Data

May 7, 2015 (KR) .......................... 10-2015-0063866

(51) Int. Cl.
*A61B 8/00* (2006.01)

(52) U.S. Cl.
CPC .............. *A61B 8/469* (2013.01); *A61B 8/465* (2013.01); *A61B 8/467* (2013.01); *A61B 8/54* (2013.01); *A61B 8/4405* (2013.01)

(58) Field of Classification Search
CPC ....... A61B 8/13; A61B 8/4405; A61B 8/4472; A61B 8/4477; A61B 8/465; A61B 8/467; A61B 8/469; A61B 8/54
USPC ....................................................... 600/437
See application file for complete search history.

(56) References Cited

U.S. PATENT DOCUMENTS

| | | | |
|---|---|---|---|
| 6,468,212 B1 * | 10/2002 | Scott ......................... | A61B 8/00 600/437 |
| 7,158,123 B2 | 1/2007 | Myers et al. | |
| 9,877,699 B2 * | 1/2018 | Chiang ................. | G16H 30/20 |
| 2009/0043195 A1 * | 2/2009 | Poland ..................... | A61B 8/00 600/437 |
| 2010/0049046 A1 * | 2/2010 | Peiffer ..................... | A61B 8/13 600/443 |
| 2010/0062803 A1 | 3/2010 | Yun et al. | |
| 2010/0298701 A1 | 11/2010 | Shin | |
| 2010/0321324 A1 * | 12/2010 | Fukai ....................... | A61B 8/00 345/173 |

(Continued)

FOREIGN PATENT DOCUMENTS

| | | |
|---|---|---|
| KR | 10-2010-0028862 A | 3/2010 |
| KR | 10-2010-0110893 A | 10/2010 |
| KR | 10-1167248 B1 | 7/2012 |

*Primary Examiner* — Baisakhi Roy
(74) *Attorney, Agent, or Firm* — Jefferson IP Law, LLP

(57) ABSTRACT

An ultrasound diagnosis apparatus for emitting ultrasound waves to an examination object and obtaining an ultrasound image is provided. The apparatus includes a touch display configured to display a screen that includes the ultrasound image, and a controller configured to receive a touch input associated with the ultrasound image, and set a focus or depth of the ultrasound image to be displayed based on a touched position.

20 Claims, 58 Drawing Sheets

(56) References Cited

U.S. PATENT DOCUMENTS

2014/0276069 A1* 9/2014 Amble ............... A61B 8/5207
                                                    600/447

* cited by examiner

100

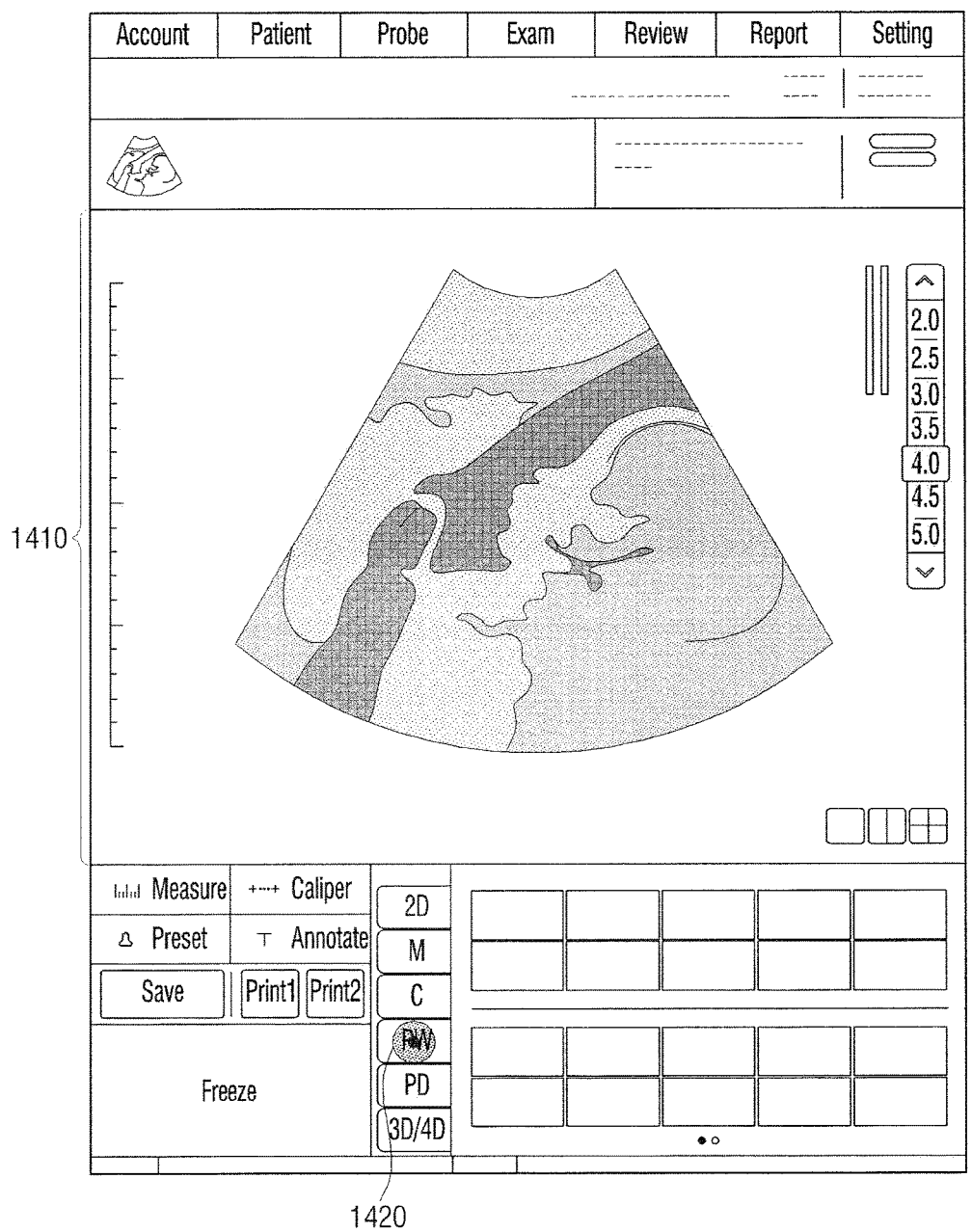

ULTRASOUND DIAGNOSIS APPARATUS AND CONTROL METHOD THEREOF

CROSS-REFERENCE TO RELATED APPLICATION(S)

This application claims the benefit under 35 U.S.C. § 119(e) of a U.S. provisional application filed on Nov. 4, 2014, in the U.S. Patent and Trademark Office and assigned Ser. No. 62/074,834, and under 35 U.S.C. § 119(a) of a Korean patent application filed on May 7, 2015 in the Korean Intellectual Property Office and assigned serial number 10-2015-0063866, the entire disclosure of which is hereby incorporated by reference.

TECHNICAL FIELD

The present disclosure relates to methods and apparatuses consistent with the various embodiments of an ultrasound diagnosis apparatus and a control method thereof. More particularly, the present disclosure relates to an ultrasound diagnosis apparatus that provides a new interface to photograph or manipulate an ultrasound image and a control method thereof.

BACKGROUND

An ultrasound diagnosis apparatus is a main diagnosis apparatus capable of observing a lesion inside a patient in medical fields.

An ultrasound diagnosis apparatus is an apparatus configured to emit high frequency sound waves in inaudible ranges from outside to inside a patient's body and to receive sound waves being reflected from the body so as to generate images. Modern high performance ultrasound diagnosis apparatuses have advanced to display not only 2-dimensional tomographic images of inside a subject body but also to generate and display 3-dimensional images thereof.

An ultrasound diagnosis apparatus is equipped with a display for displaying ultrasound images and a control panel having multiple input buttons or dial buttons and the like to control the functions of the ultrasound diagnosis apparatus according to the related art.

In order to use the ultrasound diagnosis apparatus, a user must be well aware of the locations and manipulating methods associated with the buttons in the control panel. Not only that, a user has to overcome the difficulty to carefully control the analog type buttons while watching the display according to the related art.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide an ultrasound diagnosis apparatus equipped with a new type of interface for photographing and manipulating ultrasound images and a control method thereof.

In accordance with an aspect of the present disclosure, an ultrasound diagnosis apparatus for emitting ultrasound waves to an examination object and obtaining an ultrasound image is provided. The apparatus includes a touch display configured to display a screen that includes the ultrasound image, and a controller configured to receive a touch input associated with the ultrasound image and set a focus or depth of the ultrasound image to be displayed based on a touched position.

The controller is further configured to set a focus region at a depth corresponding to the touched position to be in focus so as to change a resolution of the ultrasound image when the touch input associated with the ultrasound image is received.

The controller is further configured to: in response to receiving the touch input at a first corner from among two corner regions parallel to a depth direction of the ultrasound image, set the focus of the ultrasound image corresponding to the touched position on the first corner, and in response to receiving the touch input at a second corner, set the depth of the ultrasound image to be displayed corresponding to the touched position on the second corner to be displayed.

The controller is further configured to, in response to receiving the touch input of dragging a corner region at an end of a depth direction of the ultrasound image displayed, set the depth of the ultrasound image to be displayed according to a position associated with a location in which the first or second corner region is dragged.

The controller is further configured to display a manipulating point on each of a plurality of depth regions that configure the ultrasound image and in response to receiving the touch input within a depth region associated with one of the plurality of manipulating points, move the one manipulating point in predetermined units, and change a total gain compensation (TGC) according to a distance and direction by which the manipulating point is moved.

The controller is further configured to, in response to receiving the touch input of dragging within the depth region, move the manipulating point within the depth region where the drag is detected in smaller units than the distance by which the touched point is moved by the drag.

The controller is further configured to, in response to receiving the touch input of tapping within the depth region, move the manipulating point within the depth region where the tapping is detected in the predetermined units based on a number of times the touch input of tapping is received.

The controller, in response to a predetermined event occurring, is further configured to display a still image of the ultrasound image, display a mark on the point where a touch is detected in the still ultrasound image, and in response to detecting a touch in another point with the touch of the still ultrasound image being retained, fixate the position of the displayed mark.

The controller is further configured to display an expanded image of a periphery associated with the point where the touch is detected in the still ultrasound image, display a mark on the expanded image, where the mark corresponds to the point where the touch is detected in the still ultrasound image, and in response to the touch on the still ultrasound image being dragged, move the mark within the expanded image.

The controller is further configured to move the mark within the expanded region in smaller units than the distance by which the touched point is moved by the drag.

In accordance with an aspect of the present disclosure, a method of controlling an ultrasound diagnosis apparatus for emitting ultrasound waves to an examination object and obtaining an ultrasound image is provided. The method includes displaying a screen that includes the ultrasound image, receiving a touch input associated with the ultrasound image, and setting a focus or depth of the ultrasound image to be displayed based on a touched position.

The setting of the focus, in response to receiving the touch input associated with the ultrasound image, may set a focus region at a depth corresponding to the touched position to be in focus so as to change a resolution of the ultrasound image.

The setting of the focus, in response to receiving a touch input at a first corner from among two corner regions parallel to a depth direction of the ultrasound image, may set the focus of the ultrasound image corresponding to the touched position on the one corner, and in response to receiving the touch input at a second corner, set the depth of the ultrasound image to be displayed corresponding to the touched position on the second corner to be displayed.

The setting of the focus, in response to receiving the touch input of dragging a corner region at an end of a depth direction of the ultrasound image displayed, may set the depth of the ultrasound image to be displayed according to a position to which the corner region is dragged.

The setting of the focus may further comprises displaying a manipulating point on each of a plurality of depth regions associated with the ultrasound image, and the method may further includes in response to receiving the touch input within a depth region associated with to one of the plurality of manipulating points, moving the one manipulating point in predetermined units, and changing a TGC based on a distance and direction by which the manipulating point is moved.

The moving of the one manipulating point, in response to receiving the touch input of dragging within the depth region, may move the manipulating point within the depth region where the drag is detected in smaller units than the distance by which the touched point is moved by the drag.

The moving of the manipulating point, in response to receiving a touch input of tapping within the depth region, may move the manipulating point within the depth region where the tapping is detected in the predetermined units according to a number of times the touch input of tapping is received.

The method may further include in response to a predetermined event occurring, displaying a still image of the ultrasound image, displaying a mark on a first point where a touch is detected in the still ultrasound image, and in response to detecting a touch at a second point with the touch associated with the first point being retained, fixating the position of the displayed mark.

The method may further include displaying an expanded image of a periphery of the point where the touch input is detected in the still ultrasound image, displaying a mark on the expanded image, where the mark associated with the point where the touch input is detected in the still ultrasound image, and in response to the touch on the still ultrasound image being dragged, moving the mark within the expanded image.

The moving of the mark within the expanded image includes may move the mark within the expanded region in smaller units than the distance by which the touched point is moved by the drag.

According to the aforementioned various embodiments of the present disclosure, a user may manipulate the ultrasound diagnosis apparatus more easily and intuitively.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which:

FIGS. 14A to 14C are views illustrating where the manipulation of FIG. 13A has been applied according to an embodiment of the present disclosure;

Throughout the drawings, like reference numerals will be understood to refer to like parts, components, and structures.

DETAILED DESCRIPTION

Figure 1:
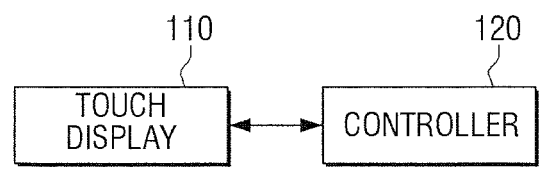
FIGS. 1 and 2 are block diagrams illustrating a configuration of an ultrasound diagnosis apparatus according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In the following description, like drawing reference numerals are used for the like elements, even in different drawings. The matters defined in the description, such as detailed construction and elements, are provided to assist in a comprehensive understanding of various embodiments of the present disclosure. However, various embodiments of the present disclosure can be practiced without those specifically defined matters. Also, well-known functions or constructions are not described in detail since they would obscure the application with unnecessary detail.

Terms such as 'first' and 'second' may be used to describe various components, but they should not limit the various components. Those terms are only used for the purpose of differentiating a component from other components. For example, a first component may be referred to as a second component, and a second component may be referred to as a first component and so forth without departing from the spirit and scope of the present disclosure. In addition, 'and/or' may include any one of or a combination of the components mentioned.

In addition, a singular form may include a plural from as long as it is not specifically mentioned in a sentence. In addition, "include/comprise" or "including/comprising" used in the specification represents that one or more components, operations, and elements exist or are added.

In the embodiments of the present disclosure, a 'module' or 'unit' performs at least one function or operation, and may be realized as hardware or software, or a combination thereof. In addition, a plurality of 'modules' or a plurality of 'units' may be integrated into at least one module and be realized as at least one processor (not illustrated) except for when they need to be realized as a certain hardware.

Figure 2:
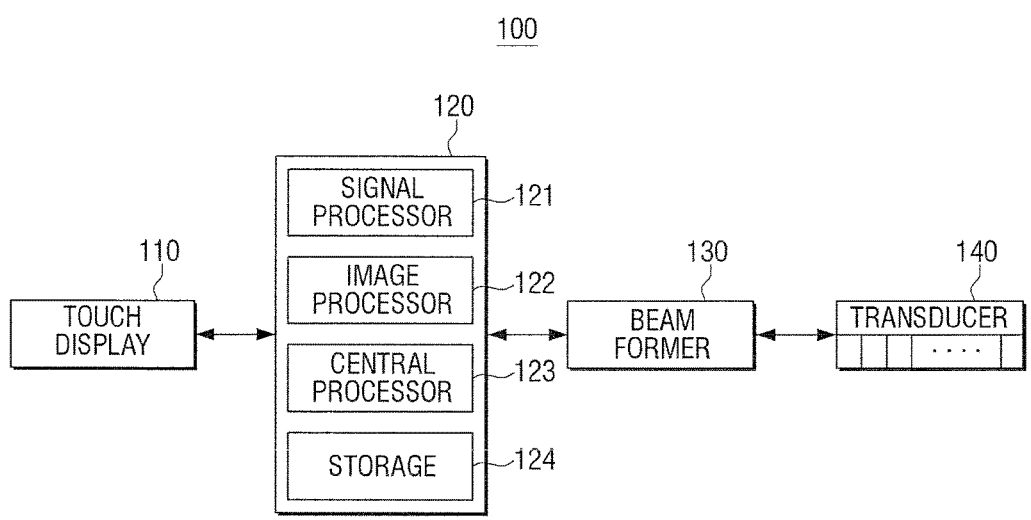

FIGS. 1 and 2 are block diagrams illustrating a configuration of an ultrasound diagnosis apparatus according to an embodiment of the present disclosure.

Referring to FIG. 1, the ultrasound diagnosis apparatus 100 includes a touch display 110 and controller 120.

The touch display 110 detects a touch and displays an image on a screen. More specifically, the touch display 110 may output a rendered image data visually, and at the same time detect a contact (touch) of a user's body part or touch input apparatus on the screen.

The touch display 110 displays a user interface screen and detects a touch on the interface screen thereby providing the user with the intuitiveness of directly manipulating and/or interacting with the interface through the screen.

The touch display 110 may display not only an ultrasound image and the interface screen but also various types of screens such as a booting screen, an alarm screen, and the like.

The touch display 110 may include a touch unit for sensing a touch input and a display unit for displaying an interface and/or an image on a screen. In an exemplary embodiment, the touch unit and display unit may be coupled to each other (e.g., deposited on top of each other) or integrated with each other as a single device. The touch unit may include a touch sensor for sensing a touch input and a proximity sensor for sensing an approaching of a user's touch. The display unit may use a cathode ray tube (CRT) or various types of flat panel displays (FPD) such as a liquid crystal display (LCD) panel and the like.

The controller 120 is configured to control each component of the ultrasound diagnosis apparatus 100. More specifically, the controller 120 may control each component of the ultrasound diagnosis apparatus 100 in order to perform a diagnosing function using ultrasound of the ultrasound diagnosis apparatus 100.

The controller 120 may process image data to be displayed on the touch display 110 graphically and provide the processed image data to the touch display 110. In addition, the controller 120 may receive a touch input detected at the touch display 110.

The controller 120 may display various interface screens on the touch display 110. Specific examples and explanation thereon will be explained later on with reference to the drawings.

The controller 120 includes at least one processor, a read-only memory (ROM) for storing a control program that controls the ultrasound diagnosis apparatus 100 and a random access memory (RAM) used to store a signal or data input from outside the ultrasound diagnosis apparatus 100 or used as a memory area for applications or operations to be performed in the ultrasound diagnosis apparatus 100. The processor may include at least one of a single core processor, a dual core processor, a triple core processor and a quad core processor. In an exemplary embodiment, at least one processor, ROM, and RAM are mutually connected through an internal bus. More detailed explanation on the configuration of the ultrasound diagnosis apparatus 100 will be made hereinafter with reference to FIG. 2.

Referring to FIG. 2, the ultrasound diagnosis apparatus 100 includes a touch display 110, a controller 120, a beam former 130, and a probe 140. The controller 120 includes a signal processor 121, an image processor 122, a central processor 123, and storage 124.

The touch display 110 has the same configuration and operation methods as the touch display 110 of FIG. 1 and thus repeated explanation will not be made.

The probe 140 includes a plurality of transducers. In an exemplary embodiment, each transducer transmits ultrasound waves to the examination object and then receives ultrasound waves reflected back from the examination subject.

The beam former 130 performs a transmission-focusing of the ultrasound wave being transmitted from each transducer to the examination object and performs a reception-focusing of the reflected waves emitted from the examination object to each transducer by applying a time-delay to the reflected waves.

The signal processor 121 receives a signal of a reflected wave that has been reception-focused at the beam former 130 and adjusts a gain of the signal. More specifically, the signal processor 121 sets a total gain compensation (TGC) or sensitivity time compensation (STC) of the signal by the reflected wave received.

In an exemplary embodiment, the TGC refers to controlling a gain of a reflected wave according to a depth of an organ to which ultrasound was emitted in order to alleviate the phenomenon in which the farther the organ is distanced from the body surface, the more blurry the image of the organ is since the deeper the ultrasound is emitted into the examination object, less intense the reflected ultrasound is.

The image processor 122 generates ultrasound image data. More specifically, the image processor 122 may generate ultrasound image data that may display the reflected wave signal output from the signal processor 121 on the touch display 110 as a 2-dimensional or 3-dimensional image.

The central processor 123 controls each component of the ultrasound diagnosis apparatus 100. More specifically, the central processor 123 may relay a signal being transmitted inside the controller 120 or a signal being input and output between the controller 120 and other components. In addition, the central processor 123 may perform computation operations for executing a program such as an operating system and application and the like on the ultrasound diagnosis apparatus 100 and operations of transmitting a suitable signal to each component at a command received from the user.

The storage 124 is configured to store data. More specifically, the storage 124 may store various programs and image data generated when photographing an ultrasound image.

Hereinafter, control operations and functions of the controller 120 of the ultrasound diagnosis apparatus 100 of FIGS. 1 and 2 will be explained with reference to FIGS. 3 to 5.

Figure 3:
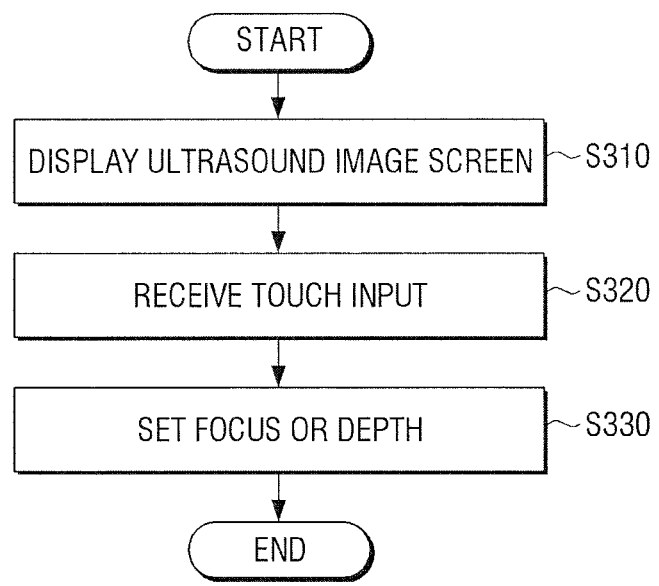
FIG. 3 is a flowchart illustrating a control method of an ultrasound diagnosis apparatus according to an embodiment of the present disclosure.

FIG. 3 is a flowchart illustrating a control method of an ultrasound diagnosis apparatus according to an embodiment of the present disclosure.

Referring to FIG. 3, a screen that includes an ultrasound image is displayed on the touch display 110 at operation 5310. More specifically, a screen for providing the ultrasound image obtained after emitting ultrasound waves to an examination subject may be displayed on the touch display 110 together with an interface.

Then, a touch input corresponding to a touch detected in the touch display 110 is received in the controller 120 at operation 5320.

In addition, the controller 120 sets a focus parameter associated with the ultrasound image or a depth of the ultrasound image being displayed based on the touched position at operation 5330.

In an exemplary embodiment, the controller 120 may set the focus parameter or the depth by determining in which part of the ultrasound image displayed on the screen of the touch display 110 the user's manipulation of touching the ultrasound image has been detected. More detailed explanation thereof will be made later on with reference to FIGS. 22 to 27.

Figure 4:
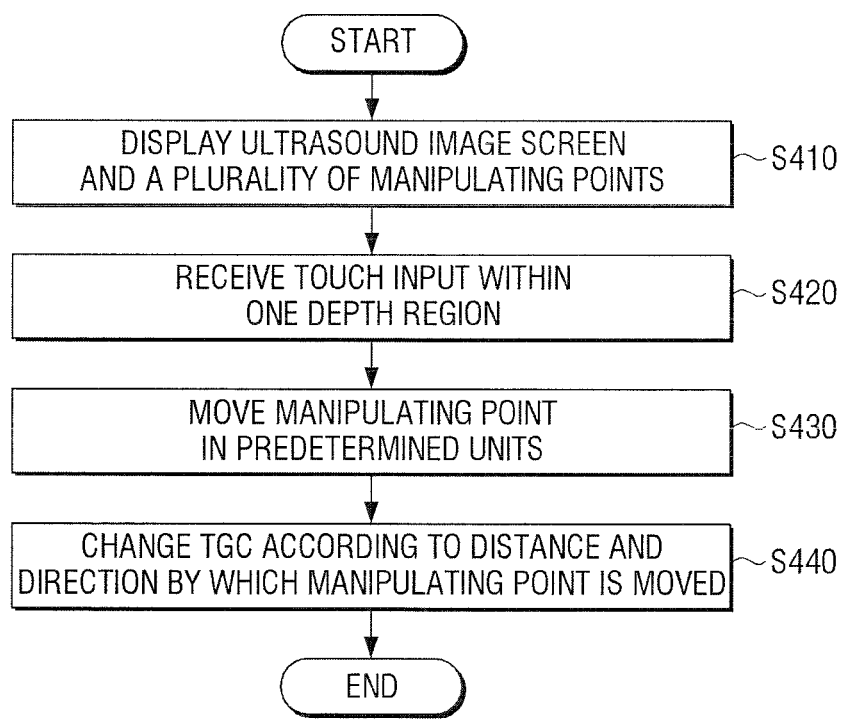
FIG. 4 is a flowchart illustrating a control method of an ultrasound diagnosis apparatus according to an embodiment of the present disclosure.

FIG. 4 is a flowchart illustrating a control method of an ultrasound diagnosis apparatus according to an embodiment of the present disclosure.

Referring to FIG. 4, on the touch display 110, a plurality of manipulating points for controlling or manipulating an ultrasound image and TCG are displayed on each of the plurality of depth regions that form the ultrasound image at operation 5410. More specifically, the controller 120 may set the divided depth regions per each predetermined depth on the ultrasound image. In addition, the controller 120 may provide manipulating points for adjusting a gain of a wave reflected from the plurality of divided depth regions at each depth region.

Then, the controller 120 receives a touch input of a touch made within a depth region where one of the manipulating points displayed on the touch display 110 belongs to at operation 5420. More specifically, the touch display 110 detects a user's touch in one of the plurality of depth regions and the controller 120 may receive a signal indicative of the touch input of the detected touch.

In addition, the controller 120 moves the manipulating point associated with the touched depth region in predetermined units at operation 5430. More specifically, the controller 120 may move the manipulating point associated with the depth region where the touch input was detected in predetermined units. In an exemplary embodiment, the controller 120 may vary the direction in which to move the manipulating point depending on whether the touched position is at a left or right side of the manipulation point. In addition, the controller 120 may move the manipulating point in predetermined units and directions based on the depth and position where the touch was detected. More detailed explanation will be made later on with reference to FIGS. 28 and 29.

The controller 120 changes the TGC according to the distance and direction by which the manipulating point was moved at operation S440. For example, the controller 120 may set a gain of the reflected wave corresponding to the depth region where the manipulating point is located according to the distance and direction by which the manipulating point was moved with respect to a central axis which is used as a reference.

Figure 5:
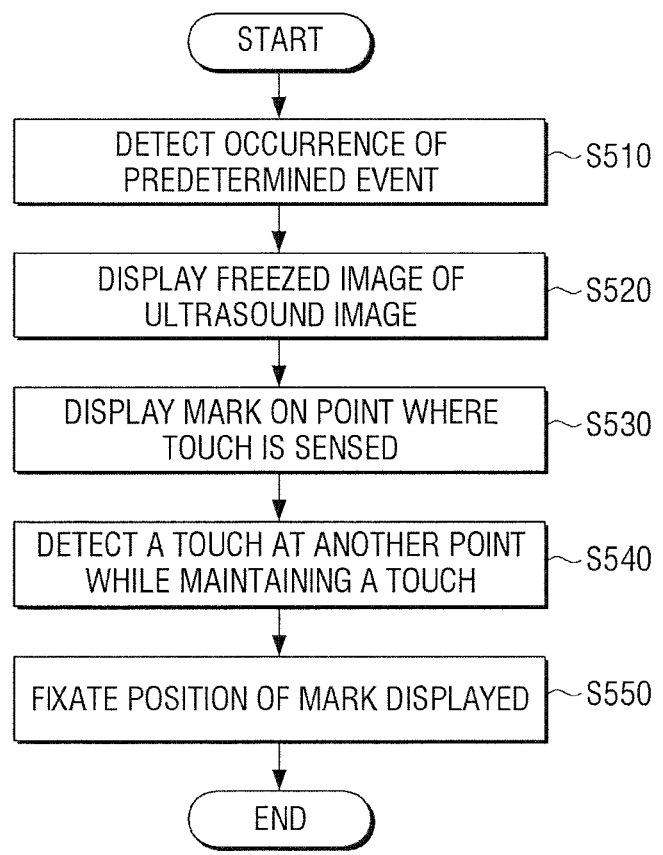
FIG. 5 is a flowchart illustrating a control method of an ultrasound diagnosis apparatus according to an embodiment of the present disclosure.

FIG. 5 is a flowchart illustrating a control method of an ultrasound diagnosis apparatus according to an embodiment of the present disclosure.

Referring to FIG. 5, the controller 120 receives a signal that a predetermined event has been detected at operation S510. For example, the controller 120 may receive a signal that represents that an event of touching a FREEZE button on the touch display 110 has occurred.

The touch display 110 displays a still image of the ultrasound image at operation S520. More specifically, the controller 120 may control the touch display 110 such that a still image of the ultrasound image is displayed. The still image may be an ultrasound image photographed when the event occurred.

The touch display 110 displays a mark on a point where the touch was detected at operation S530. More specifically, when a touch input is received, the controller 120 may control the touch display 110 such that a mark is displayed on the point where the touch was detected. In an exemplary embodiment, a mark refers to an object for marking a point where a lesion such as cancer is observed on a still ultrasound image in order to measure the size of the lesion.

The touch display 110 may detect another touch input from a different point while maintaining a former touch input at operation S540. More specifically, when a mark is positioned at a point to display the mark through an initial touch in the touch display 110, when a second touch is made at another point with the initial touch maintained, the touch display 110 may sense the user's multi touch manipulation.

The controller 120 may fix the mark displayed at operation S550. More specifically, when a second touch input is received, the controller 120 may fix the position of the mark displayed while maintaining the first touch. More detailed explanation thereof will be made later on with reference to FIGS. 30 and 31.

Such a control method of an ultrasound diagnosis apparatus according to various embodiments of the present disclosure may provide a more intuitive, detailed, simple, and convenient interface environment. The control method of FIGS. 3 to 5 may be embodied in an ultrasound diagnosis apparatus having the configuration of FIG. 1 or FIG. 2. Otherwise, the control method of FIGS. 3 to 5 may be executed in one or a plurality of apparatuses each embodied with only some of the functions or only one configuration.

In addition, such a control method of an ultrasound diagnosis apparatus as aforementioned may be embodied as a program executable in at least one computer for executing the control method. In addition, such an executable program may be stored in a non-transitory computer readable record medium.

Therefore, each of the blocks of the present disclosure may be embodied as a computer recordable code on a computer readable record medium. The computer readable record medium may be a device that may store data that may be read by a computer system.

For example, the computer readable record medium may be a ROM, RAM, CD-ROM, magnetic tape, floppy disc, optical disc, optical data storing device, or an image display such as a television that includes the storing device. In addition, the computer readable code may be embodied as a computer data signal of a reflected wave.

Probe Interaction

Figure 6:
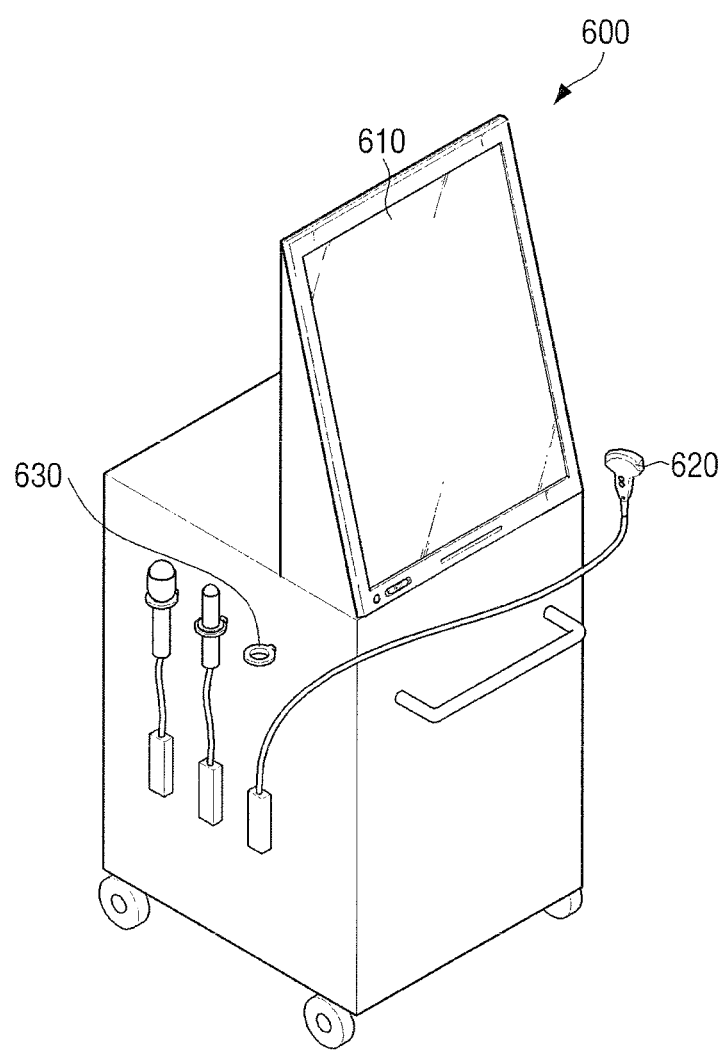
FIG. 6 is a view illustrating an appearance and automatic execution function of an ultrasound diagnosis apparatus according to an embodiment of the present disclosure.

FIG. 6 is a view illustrating an appearance and automatic execution function of an ultrasound diagnosis apparatus according to an embodiment of the present disclosure.

Referring to FIG. 6, the ultrasound diagnosis apparatus 600 is a cart type apparatus equipped with a handle and wheels so that apparatus 600 may be moved around.

A touch display 610 is provided at an upper part of the ultrasound diagnosis apparatus 600 such that that the display 610 may sense or detect a touch on any part of a screen when an image or an interface is displayed on the display.

The main body of the ultrasound diagnosis apparatus 600 may include various storage spaces, a plurality of probes 620, and a holder 630 to hang the probe. In an exemplary embodiment, the main body of the ultrasound diagnosis apparatus 600 may be further equipped with various components for communication with an external device such as various communication ports, a speaker, a gel warmer, a record medium drive, and the like.

The ultrasound diagnosis apparatus 600 may detect when the probe 620 is separated from the holder 630. More specifically, the ultrasound diagnosis apparatus 600 may generate a signal that the probe 620 has been separated from the holder 630 based on a sensor provided in the holder 630. In addition, the signal indicating that the probe 620 has been separated from the holder 630 may vary according to the type of the probe 620. Therefore, the ultrasound diagnosis apparatus 600 may also identify which probe 620 will be used by a user.

In an exemplary embodiment, the ultrasound diagnosis apparatus 600 executes an application corresponding to the identified probe 620. More specifically, when a probe for a certain use is separated, the ultrasound diagnosis apparatus 600 may automatically execute the diagnosis application suitable to the use of the separated probe.

Figure 7:
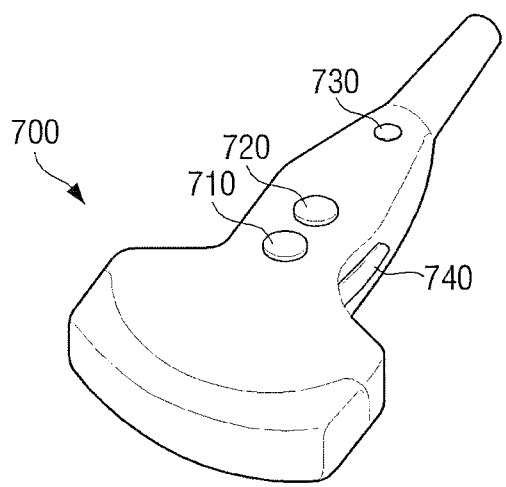
FIG. 7 is a view illustrating a structure of a probe according to an embodiment of the present disclosure.

FIG. 7 is a view illustrating a structure of a probe according to an embodiment of the present disclosure.

Referring to FIG. 7, a probe 700 includes a plurality of input means. More specifically, the probe 700 may be equipped with a plurality of buttons 710, 720, 730, 740 formed on a part of the probe 700 to be grasped by the user. For example, as illustrated in FIG. 7, the probe 700 may be equipped with a SAVE button 710, a FREEZE button 720, and a LOCK button 730 formed within an operation range manipulable by an index finger of a hand that grasps the probe 700, and a DEPTH button 740 formed within an operation range manipulable by a thumb of the hand that grasps the probe 700. In an exemplary embodiment, the SAVE button 710 may provide a function of capturing an ultrasound image, the FREEZE button 720 may provide a function of freezing or resuming photography, the LOCK button 730 may provide a function of disregarding inputting of other buttons provided in the probe 700, and the DEPTH button 740 may provide a function of adjusting the depth of an ultrasound image. One of ordinary skill in the art would recognize that a method of input utilizing physical force and/or a method of detecting a contact by a body part or motion of a body part may be applied to the input methods of the aforementioned buttons. It is also a matter of course that some of the aforementioned plurality of buttons may be omitted or a button for providing a function related to another probe may be added to the probe.

Touch Interaction for Changing Layout

Figure 8:
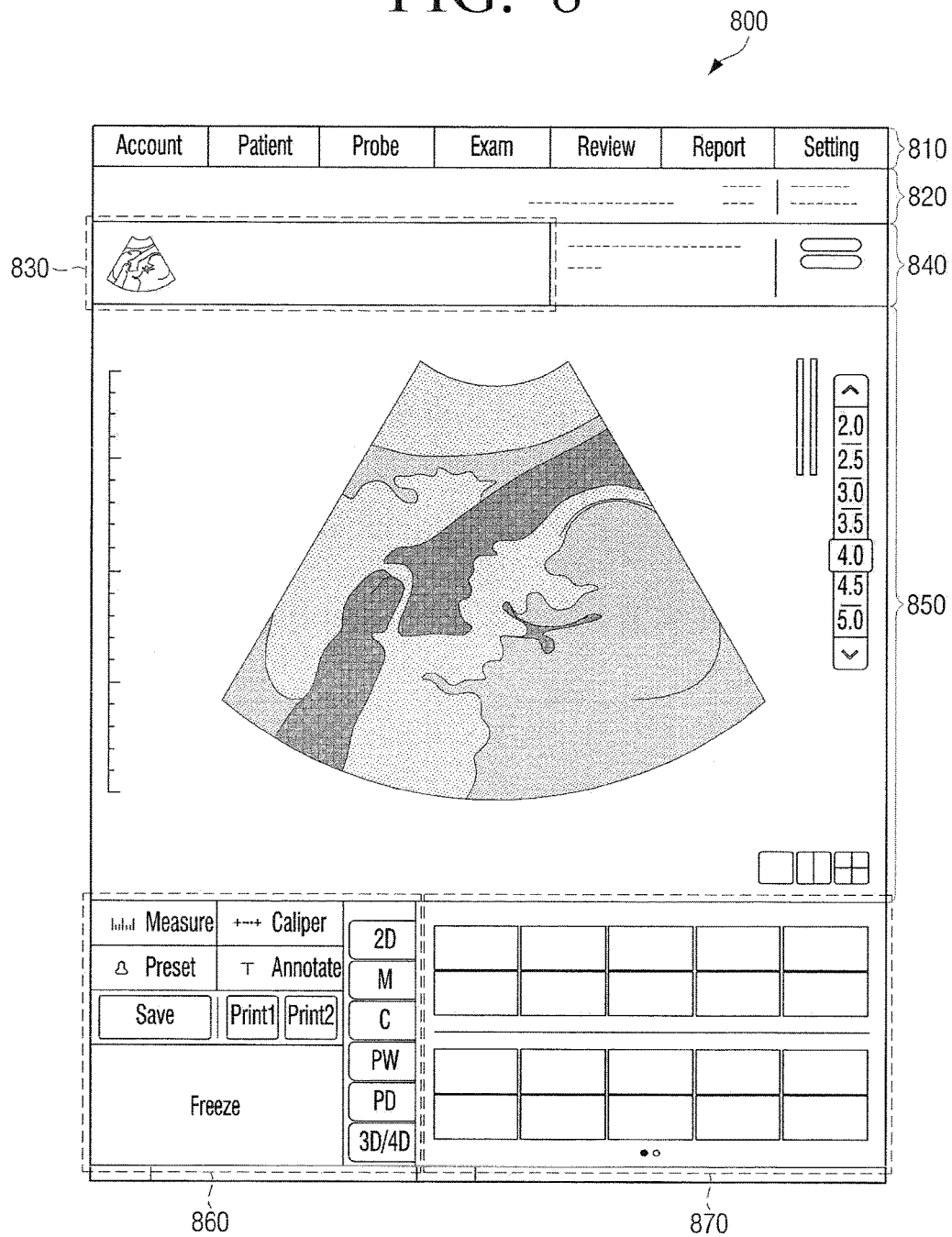
FIG. 8 is a view illustrating a layout of a screen of a full touch display according to an embodiment of the present disclosure.

FIG. 8 is a view illustrating a layout on a screen of a full touch display according to an embodiment of the present disclosure.

Referring to FIG. 8, a screen 800 is displayed on a touch display where the screen 800 is divided into a plurality of regions.

A first region 810 at an uppermost end includes a menu bar from which an option regarding an account, a patent, a probe, a diagnosis, a review, a report, and a configuration setting may be selected.

A second region 820 includes a title associated with the ultrasound imaging that includes a patient name, a hospital name, an application being executed, a photograph frame rate, information associated with the probe used in the diagnosis, sound output information, date/time information, and the like.

A third region 830 includes a thumbnail of a captured ultrasound image.

A fourth region 840 includes information on whether an ultrasound image is a 2-dimensional ultrasound image or a 3-dimensional ultrasound image, depth of the image, and focus of the image.

A fifth region 850 displays an ultrasound image being photographed or photographed together with several image setting interfaces.

A sixth region 860 provides a quick menu that includes options that are frequently used when diagnosing to help the user easily select imaging or diagnosis options.

A seventh region 870 provides a sub menu that includes various selectable options provided from the application related to the mode being executed.

Figure 9:
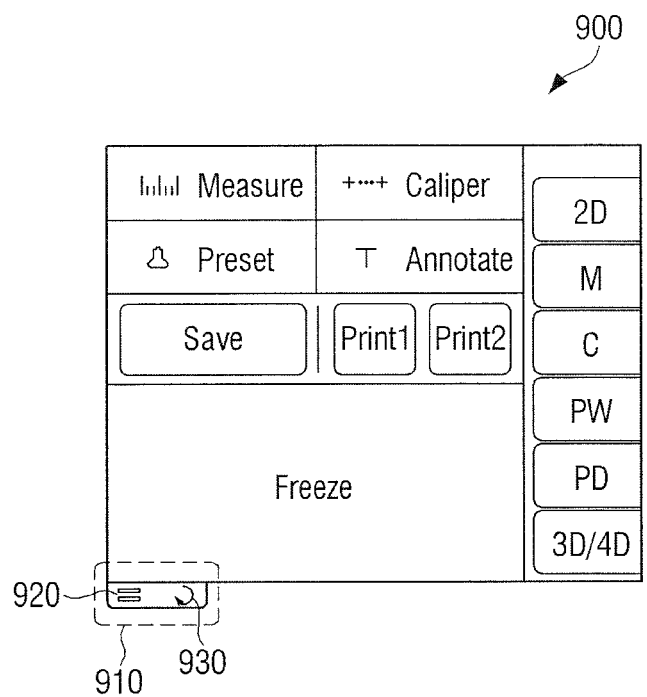
FIG. 9 is a view illustrating a sixth region included in the screen of FIG. 8 according to an embodiment of the present disclosure.

FIG. 9 is a view illustrating in detail the sixth region included in the screen of FIG. 8 according to an embodiment of the present disclosure.

Referring to FIG. 9, the sixth region 900 includes a Measure button for calculating a length, angle, and size area, a Caliper button providing a ruler function of connecting two points on an ultrasound image, a Preset button for deleting a text or indicator and the like displayed on an ultrasound image, an Annotate button for inputting a letter in any position on an ultrasound image, a Save button for capturing an ultrasound image during photographing, a Print 1 button, a Print 2 button, a Freeze button, and a plurality of Mode buttons 2D, M, C, PW, PD, 3D/4D for converting or adding an ultrasound image photographing mode.

In an exemplary embodiment, at a lowermost end of the sixth region 600, a handle 910 is provided that includes a move button 920 for the sixth region 600 and a conversion button 930 for changing an arrangement of the buttons within the sixth region 600. Referring to FIG. 10, explanation on manipulating the handle 910 will be made.

Figure 10A:
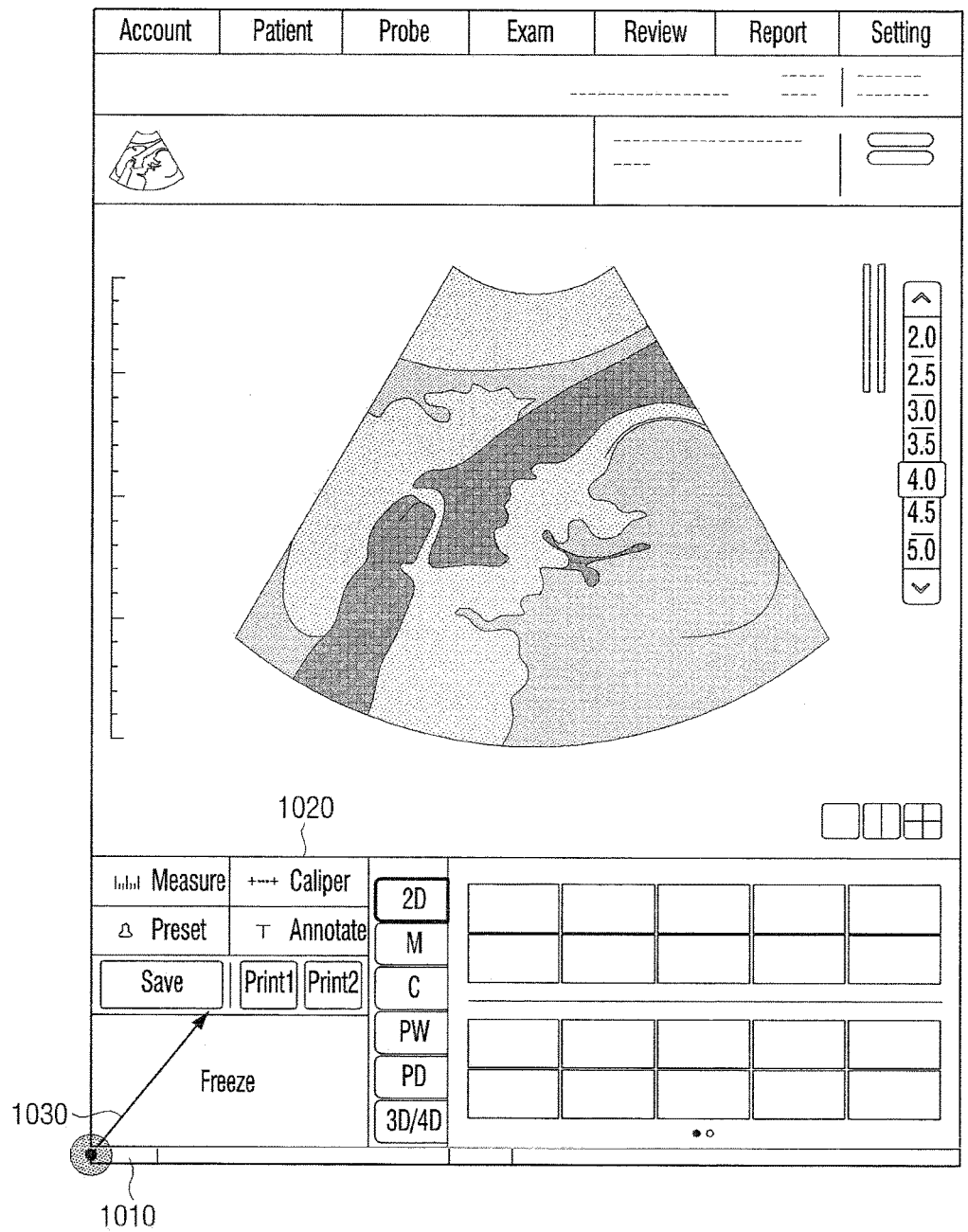
FIGS. 10A to 10C are views illustrating a manipulation of changing a state where the sixth region of FIG. 9 is being displayed on the screen of FIG. 8 according to an embodiment of the present disclosure.
Figure 10B:
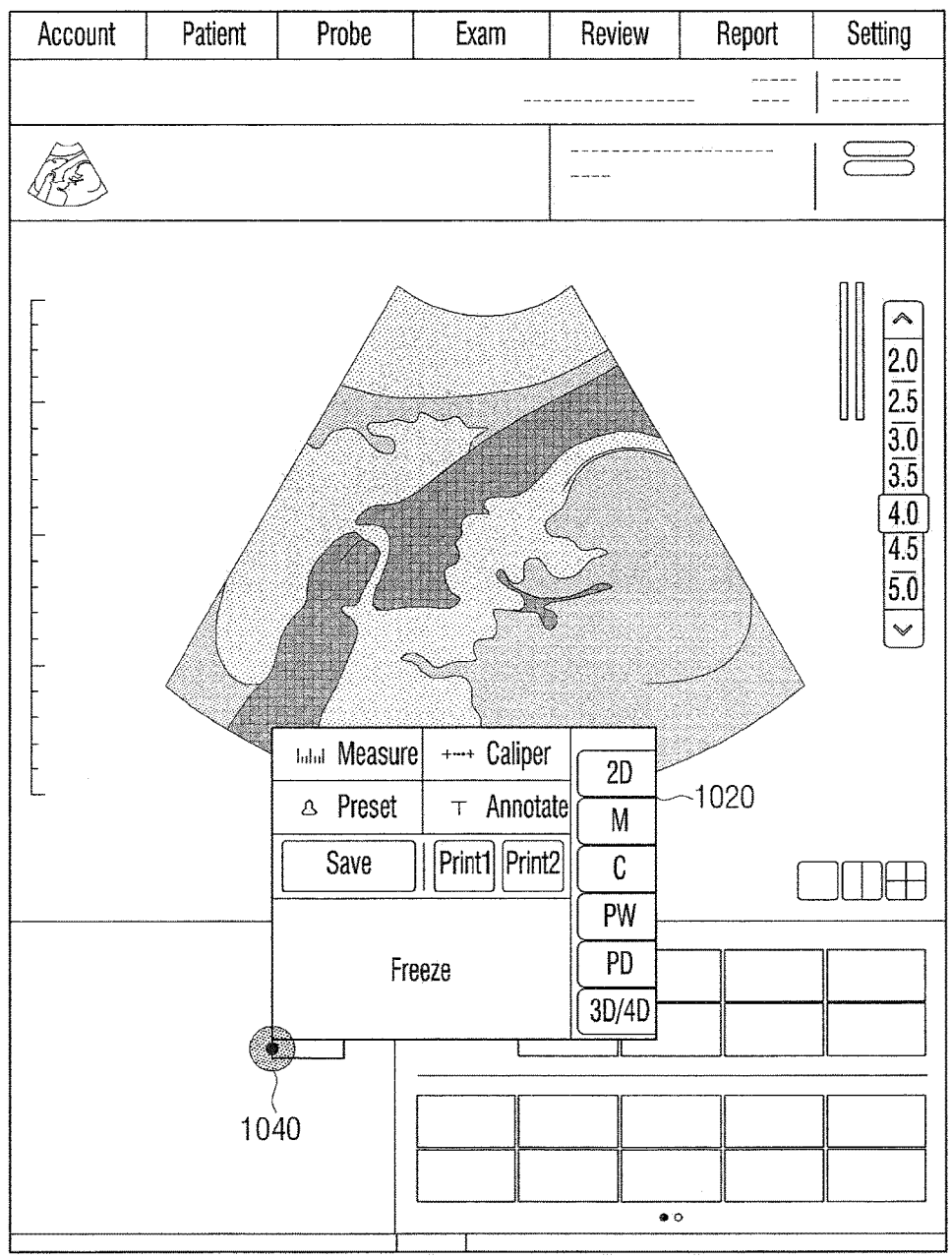
Figure 10C:
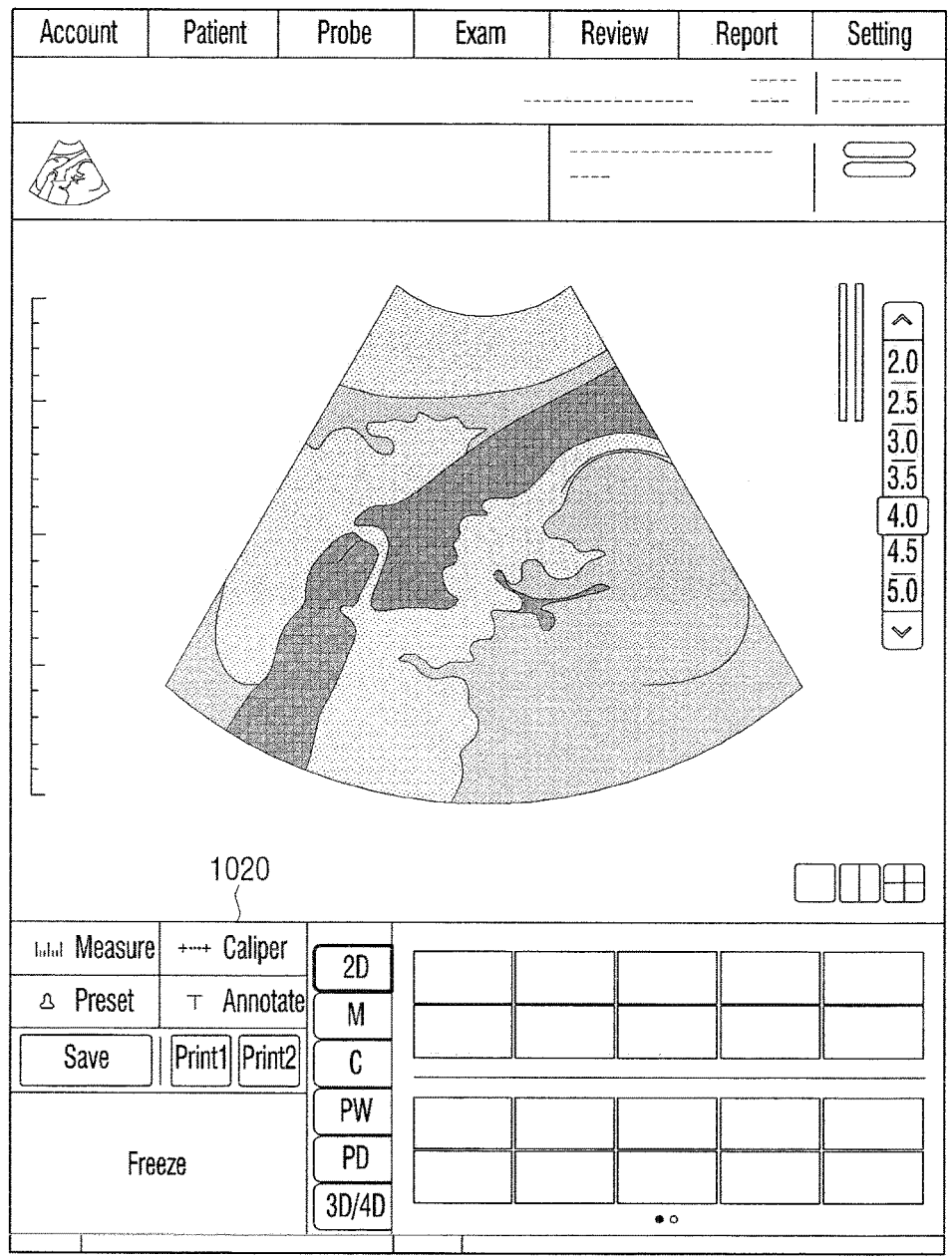

FIGS. 10A to 10C are views illustrating a manipulation of changing a state of the sixth region of FIG. 9 displayed on the screen of FIG. 8 according to an embodiment of the present disclosure.

Referring to FIG. 10A, the screen includes a plurality of regions arranged in a basic layout.

At the lower end of the sixth region 1020 where the quick menu is provided, a handle 1010 is provided.

The user may input a touch and drag 1030 manipulation of a move button of the handle 1010 through the touch display.

Referring to FIG. 10B, a state where the sixth region 1020 has been moved from a lower left end of the screen to the center of the screen by a drag manipulation input by the user is illustrated. In an exemplary embodiment, the sixth region 1020 may be displayed semi-transparently while it is being moved by the user's drag.

The user may input a double tap 1040 manipulation by tapping the position change button in the handle 1010.

Referring to FIG. 10C, a state where the sixth region 1020 has moved to the position of the initial basic layout after a double tap 1040 manipulation has been input and detected is illustrated.

Figure 11A:
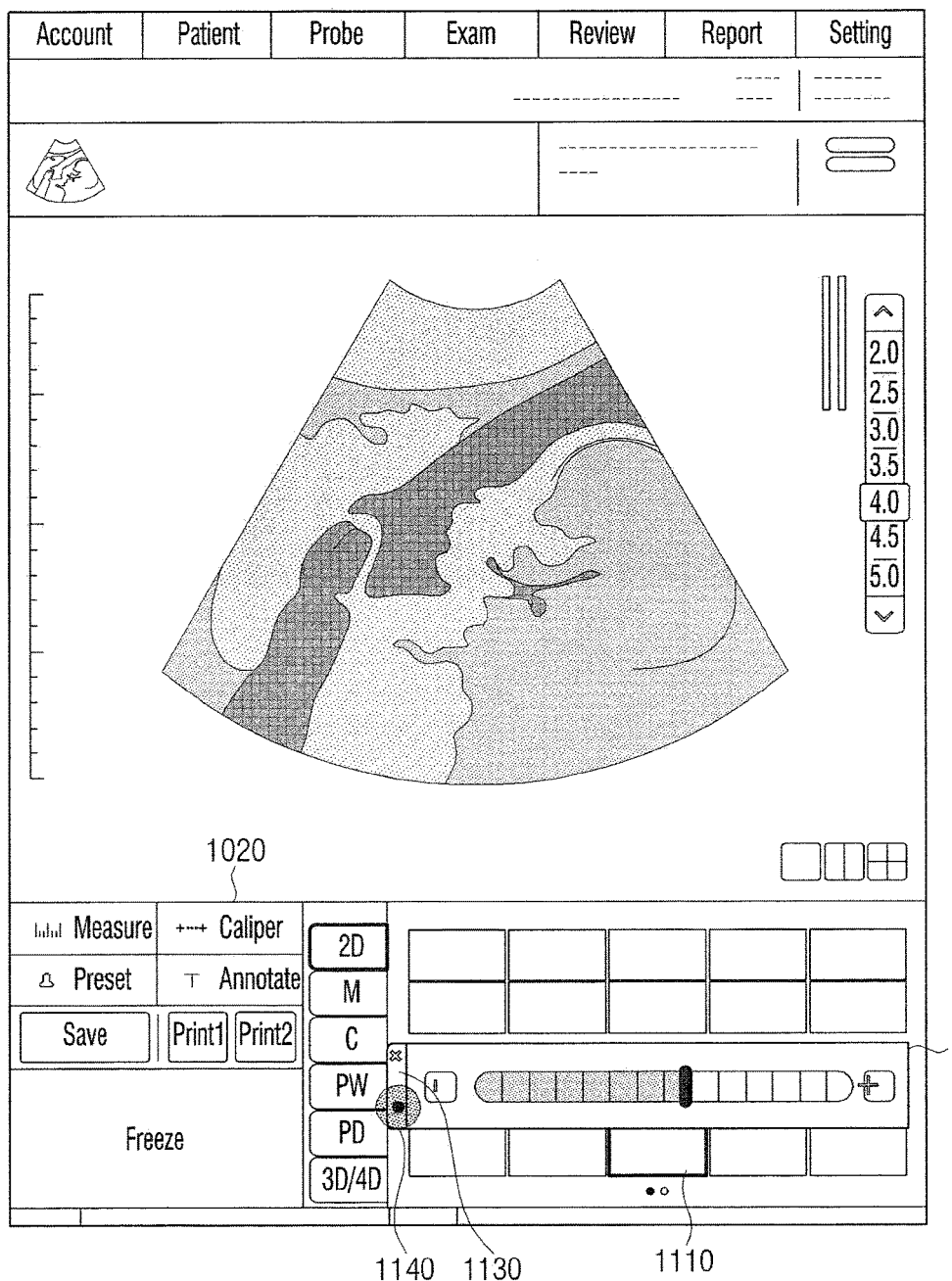
FIGS. 11A to 11C are views illustrating a manipulation of changing a state where a popup menu is being displayed on the screen of FIG. 8 according to an embodiment of the present disclosure.
Figure 11B:
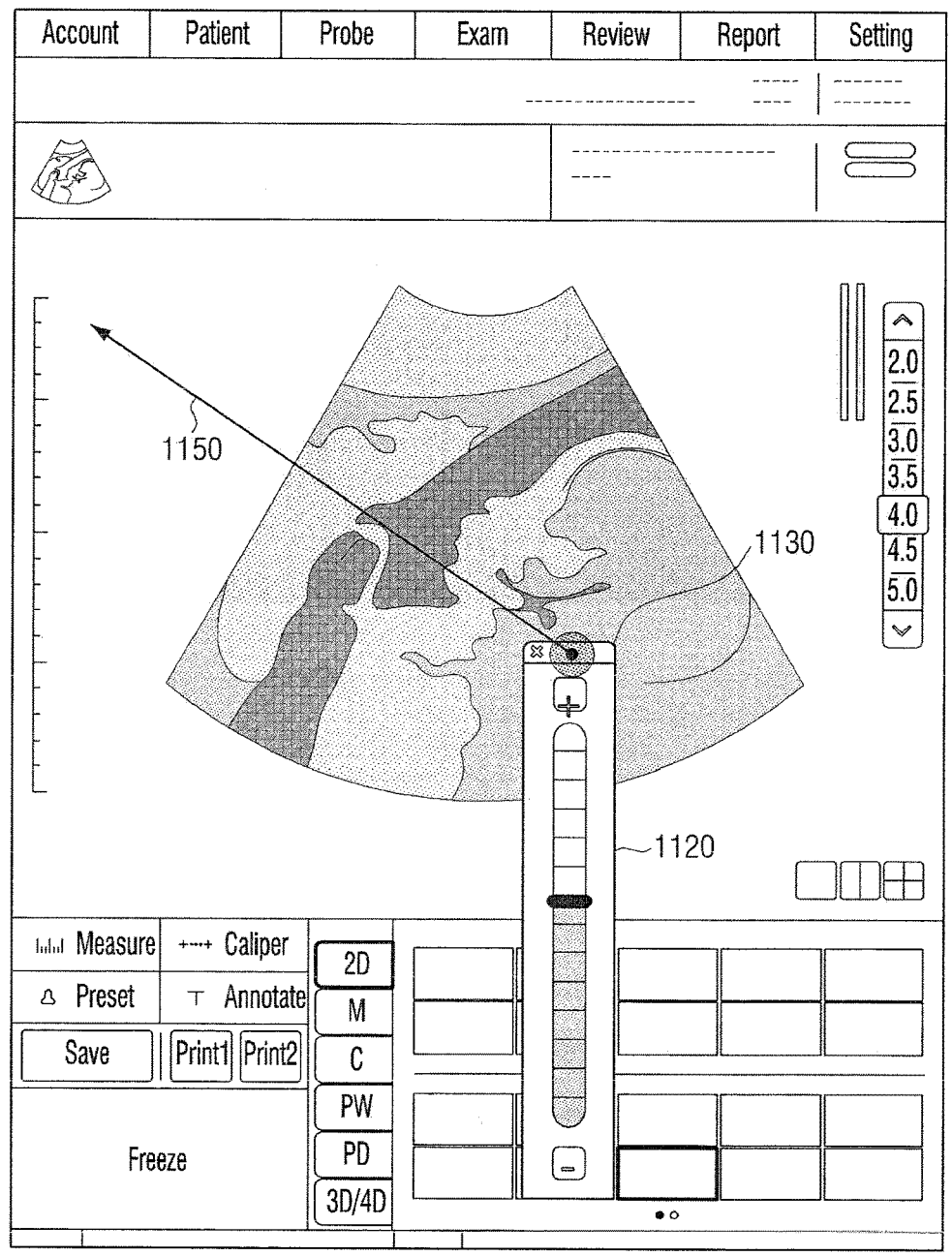
Figure 11C:
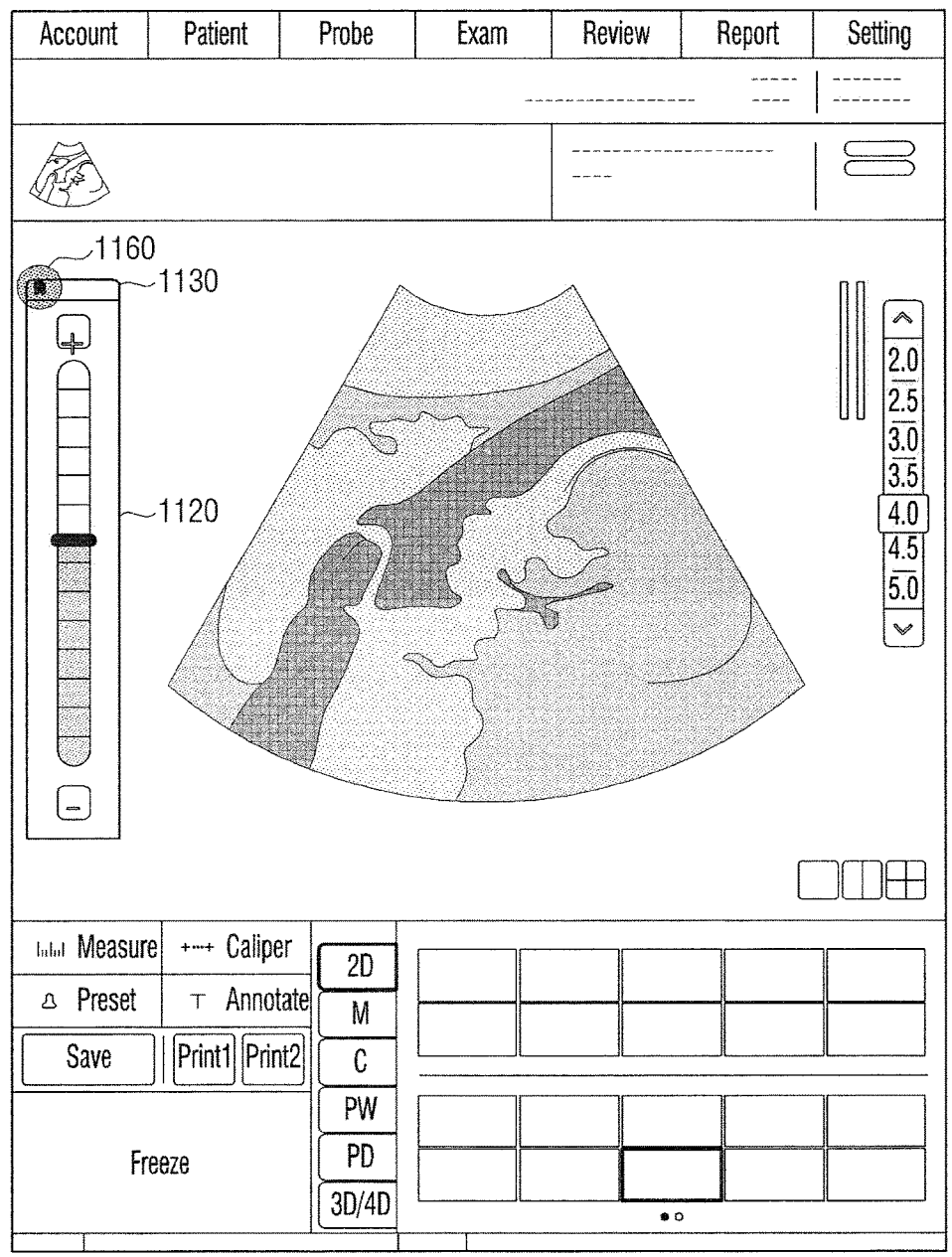

FIGS. 11A to 11C are views illustrating a manipulation of changing a state where a popup menu is displayed on the screen of FIG. 8 according to an embodiment of the present disclosure.

Referring to FIG. 11A, together with the plurality of regions arranged in the basic layout, a popup window 1120 is displayed on the screen.

In an embodiment of the present disclosure, the popup window 1120 is displayed when one option 1110 of the plurality of options of the sub menu is selected. The popup window 1120 provides an interface where the user may set a certain range.

A handle 1130 is displayed together at one side of the popup window 1120.

The user touches a rotation button 1140 on the handle 1130 of the popup window 1120.

Referring to FIG. 11B, a state where the popup window 1120 has been rotated by 90 degrees by the user's manipulation of touching the conversion button is illustrated.

The user may input a manipulation of touching and dragging 1150 a move button of the handle 1130.

Referring to FIG. 11C, a state where the popup window 1120 has been moved to where the user had input the drag manipulation is illustrated.

In an exemplary embodiment, the popup window 1120 is not displayed if the user touches a close button 1160 of the handle 1130 or if there is no user manipulation for more than a predetermined period of time.

Figure 12A:
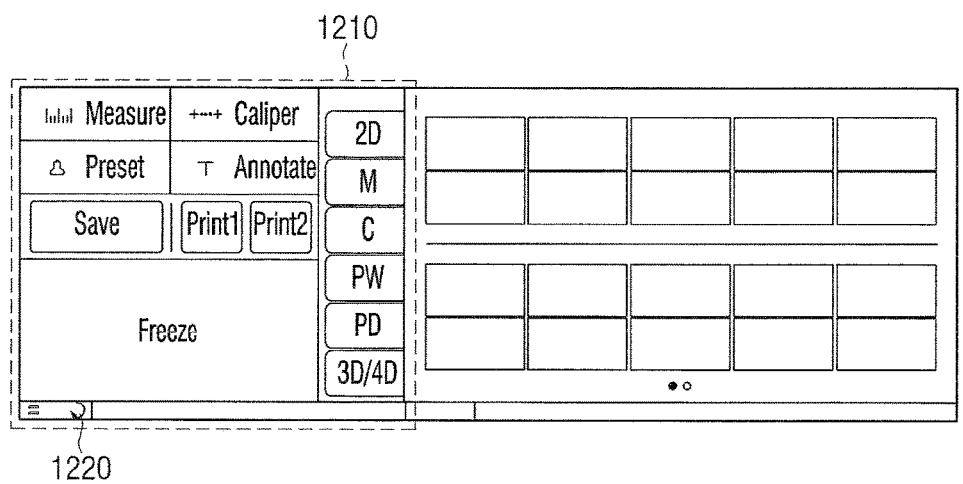
FIGS. 12A and 12B are views illustrating a manipulation of changing an arrangement of a plurality of buttons within the sixth region of FIG. 9 according to an embodiment of the present disclosure.
Figure 12B:
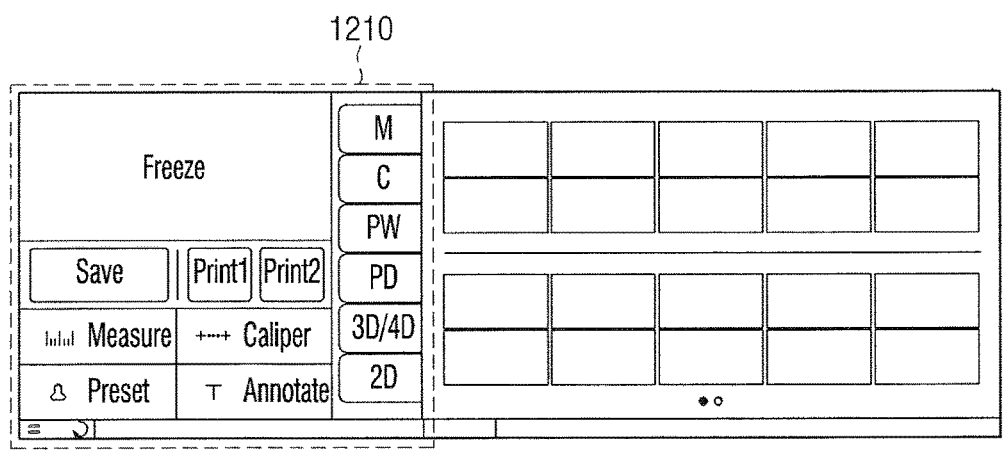

FIGS. 12A to 12B are views illustrating a manipulation of changing an arrangement of the plurality of buttons in the sixth region of FIG. 9 according to an embodiment of the present disclosure.

Referring to FIG. 12A, a state where the buttons inside the sixth region 1210 are arranged in the basic layout is illustrated.

The user may touch a conversion button 1220 on the handle at a lower end of the sixth region 1210.

Referring to FIG. 12B, a state where the buttons inside the sixth region 1210 have been arranged in another layout based on the user's manipulation of touching the conversion button 1220 is illustrated.

In an exemplary embodiment, there may be two or more layouts in which the buttons may be arranged. In addition, every time the user touches the conversion button 1220, the layout of the buttons will change to every one of the plurality of layouts in serial order.

Figure 13A:
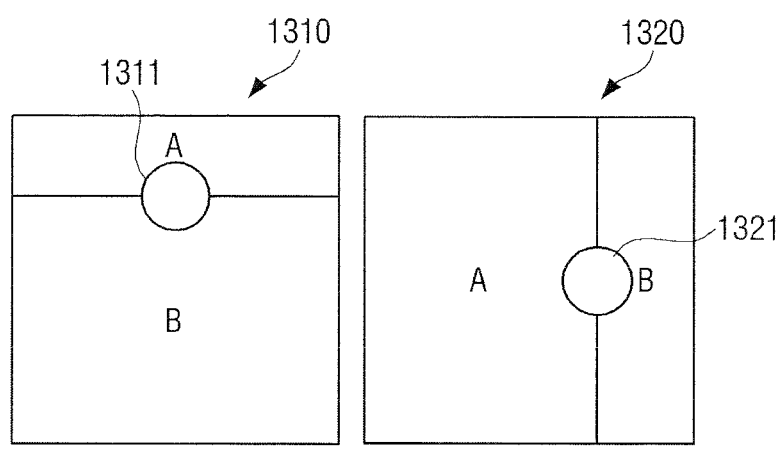
FIGS. 13A to 13C are views illustrating a manipulation of adjusting a size of each region of a screen divided into a plurality of regions according to an embodiment of the present disclosure.
Figure 13B:
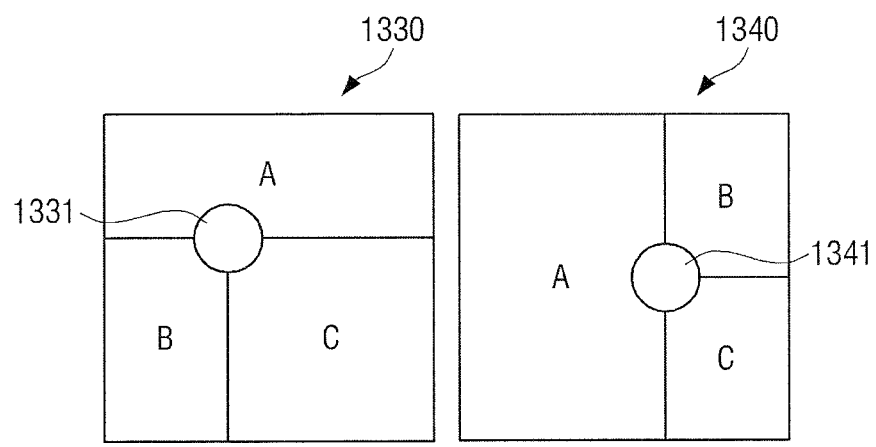
Figure 13C:
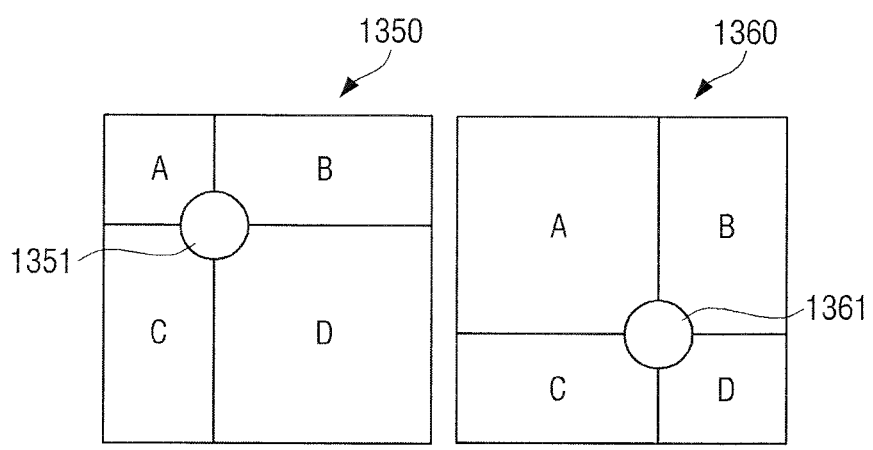

FIGS. 13A to 13C are views illustrating a manipulation of adjusting a size of each region of the screen divided into a plurality of regions according to an embodiment of the present disclosure.

Referring to FIG. 13A, screens 1310, 1320 illustrate where a region is divided into two portions A, B. The screen 1310 on the left is divided into two by a horizontal boundary line, while the screen 1320 on the right is divided into two by a vertical boundary line. By touching and dragging a boundary indicator 1311, 1321 associated with the two divided regions, one of the divided regions may be expanded as the other one is reduced.

Referring to FIG. 13B, screens 1330, 1340 illustrate where a region is divided into three portions A, B, C. The screen 1330 on the left is divided into two by a horizontal boundary line and then one of the two regions is divided again by a vertical boundary line. The screen 1340 on the right is divided into two by a vertical boundary line and then one of the two regions is divided again by a horizontal boundary line.

In an exemplary embodiment, the three divided regions may be expanded or reduced by a manipulation associated with touching and dragging an intersection indicator 1331, 1341 where the two boundary lines dividing the screen in a horizontal direction and a vertical direction meet.

Referring to FIG. 13C, screens 1350, 1360 illustrate where a region is divided into four portions A, B, C, D. The four divided regions may be expanded or reduced by a user's manipulation of touching and dragging an intersection indicator 1351, 1361 where two boundary lines crossing the screen in a horizontal direction and a vertical direction meet.

Figure 14B:
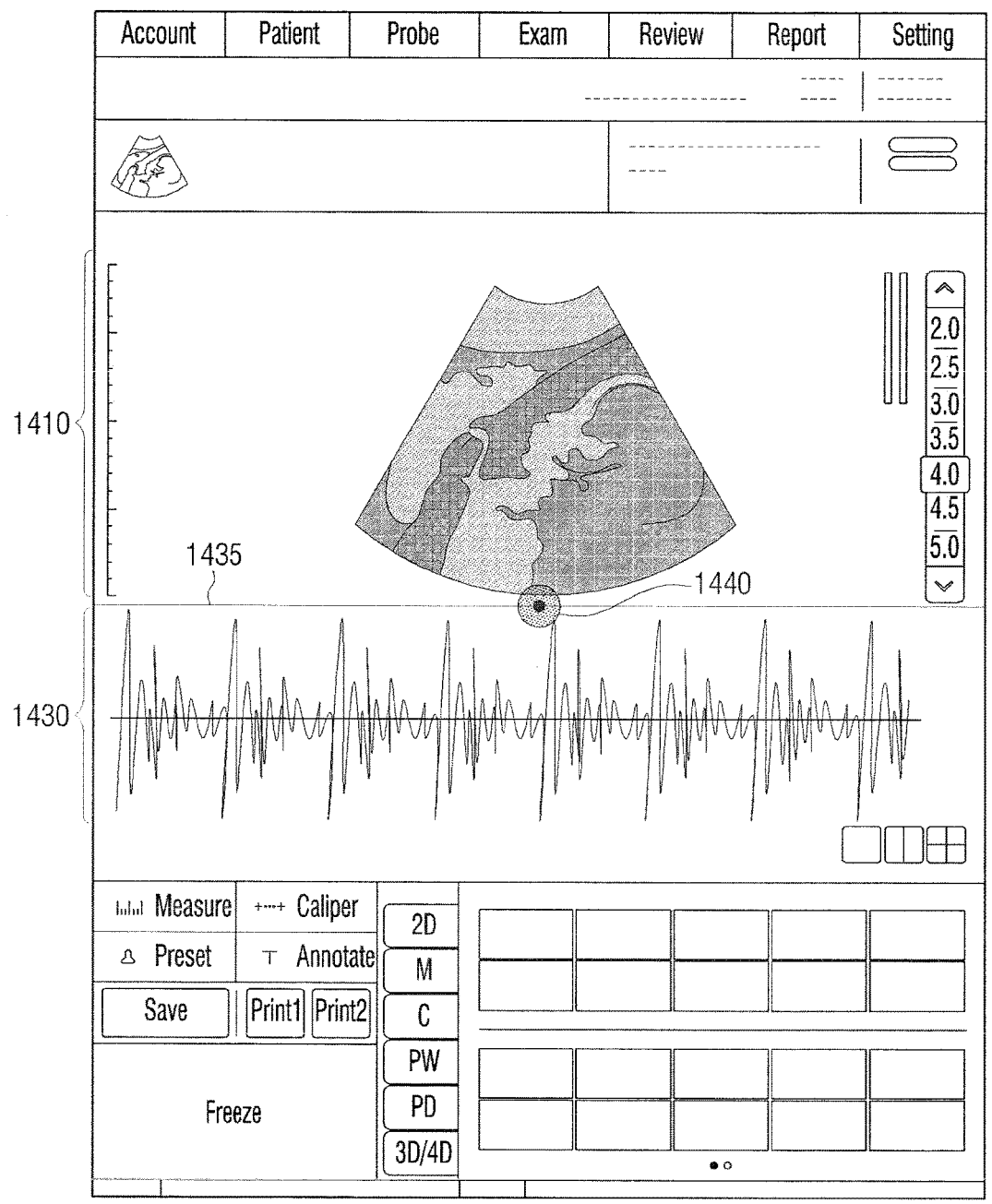
Figure 14C:
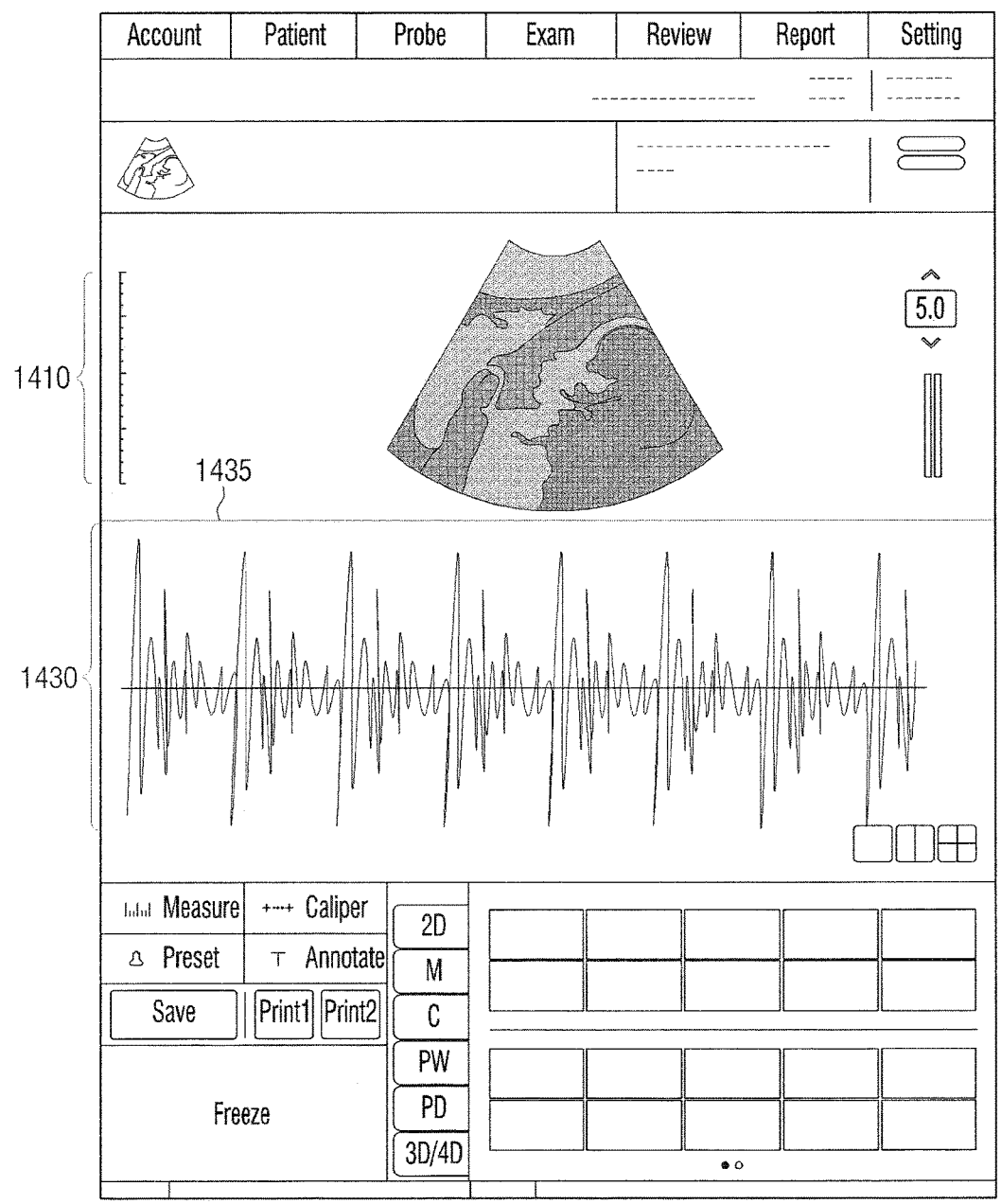

FIGS. 14A to 14C are views illustrating the application of the manipulation described in FIG. 13A according to an embodiment of the present disclosure.

Referring to FIG. 14A, an ultrasound image is being displayed on screen 1400 in an image region 1410 where a 2D/C mode has been activated.

In an exemplary embodiment, the user may touch a PW mode button 1420 to activate a 2D/C/PW complex mode.

Referring to FIG. 14B, the PW mode has been executed and screen 1400 is divided into an image region 1410 and pulsed wave image region 1430 based on an input associated with the activation of the 2D/C.PW complex mode. In addition, a boundary line 1435 is displayed in the boundary of the image region 1410 and the PW image region 1430.

Referring to FIG. 14B, in an exemplary embodiment, the user may input a manipulation 1440 by touching the boundary line displayed and providing an input associated with dragging the boundary line in an upward direction thereby increasing the area of the PW image region 1430 and decreasing the area of the image region 1410.

Referring to FIG. 14C, as the image region 1410 displayed on screen 1400 is reduced by the user's dragging manipulation, the interfaces arranged on the left and right of the ultrasound image are also reduced. In addition, the graph of the expanded PW image region 1430 is expanded as well.

It is noted that one of ordinary skill in the art would recognize that the boundary line 1435 may also be manipulated such that an input associated with dragging the boundary line in a downward direction thereby decreasing the area of the PW image region 1430 and increasing the area of the image region 1410.

Figure 15A:
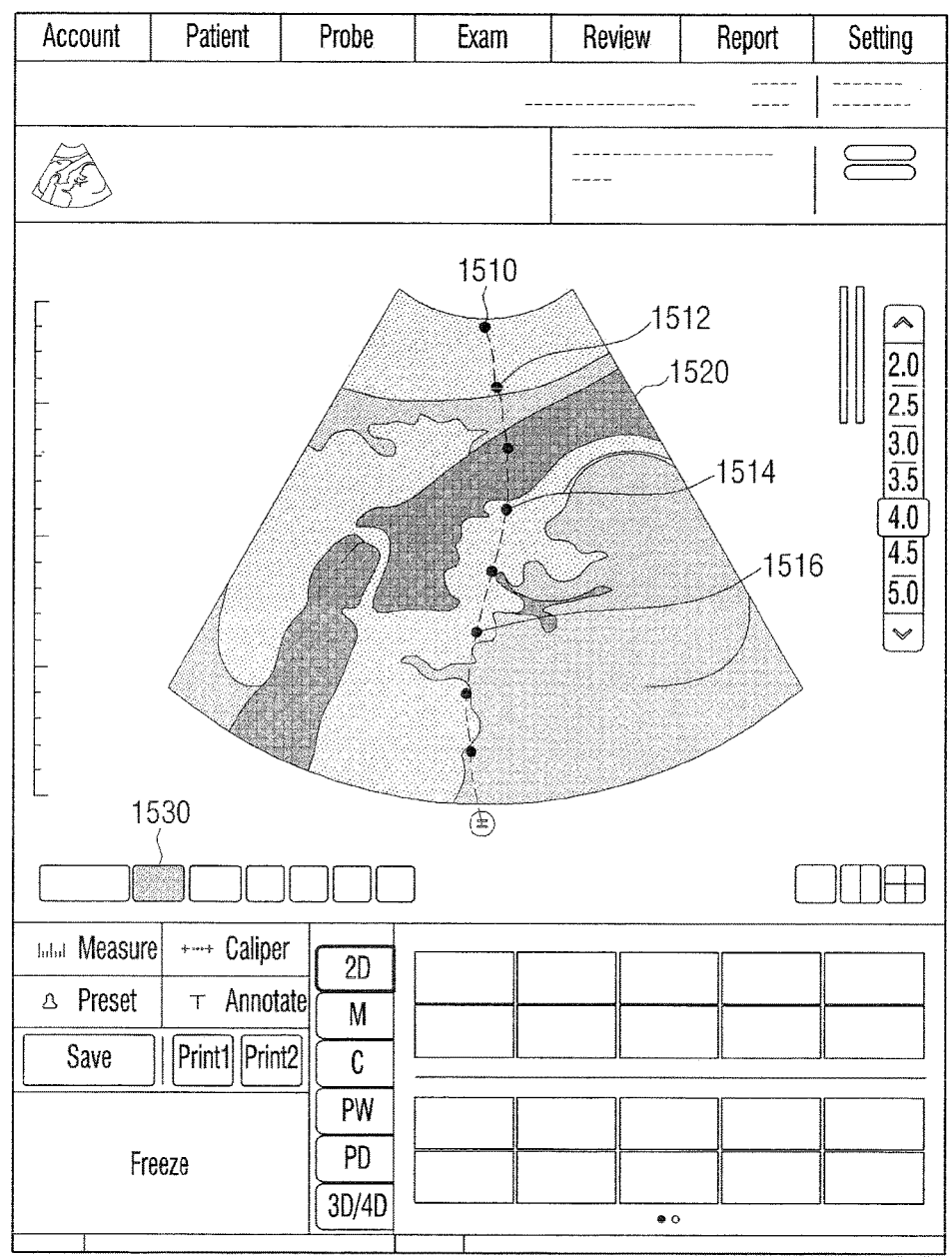
FIGS. 15A to 15C are views illustrating a manipulation of changing a position of a total gain compensation (TGC) line according to an embodiment of the present disclosure.
Figure 15B:
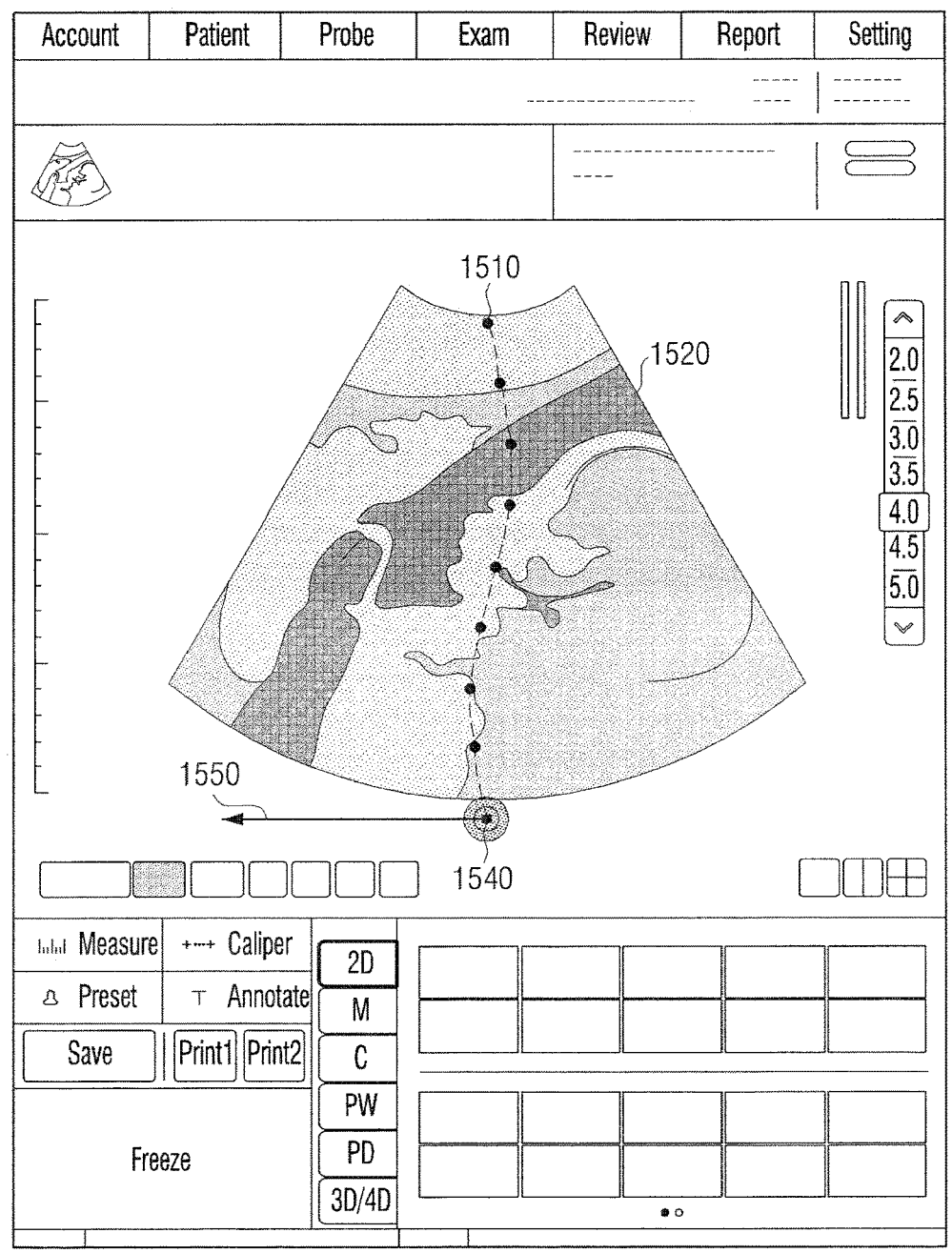
Figure 15C:
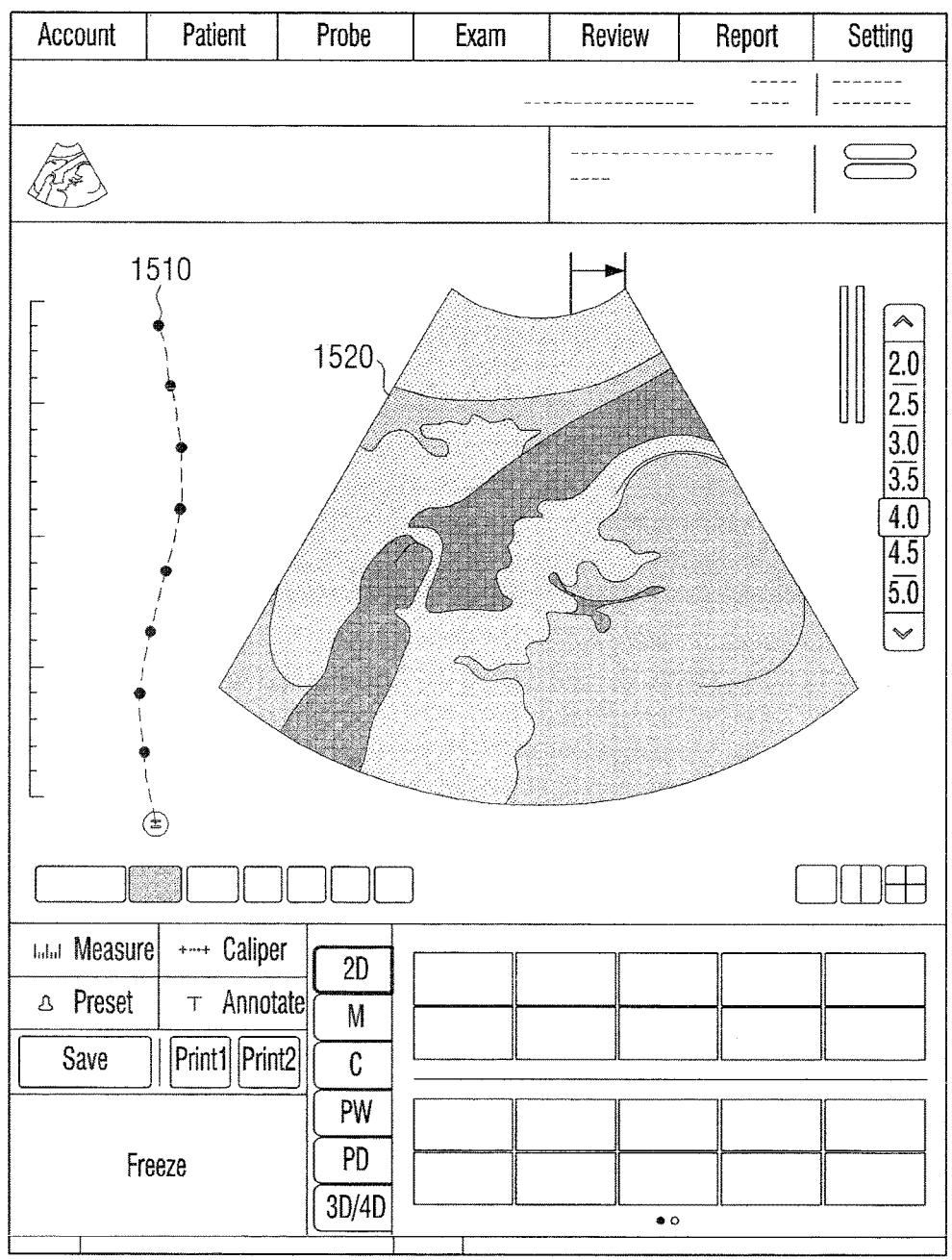

FIGS. 15A to 15C are views illustrating a manipulation of changing a position of a TGC line according to an embodiment of the present disclosure.

Referring to FIG. 15A, a screen 1500 illustrates where a touch input is detected associated with a TGC button 1530 thereby activating the TGC setting. On an image region of the screen 1500, a TGC line 1510 is displayed overlapping the ultrasound image 1520.

On the TGC line 1510, there are a plurality of manipulation points 1512, 1514, and 1516 corresponding to each of the divided depth regions according to depth of the ultrasound image.

Referring to FIG. 15B, a manipulation 1550 of touching and dragging a move button 1540 displayed on one end of the TGC line 1510 in order to change the position of the TGC line 1510 being displayed on the screen 1500 over the ultrasound image 1520 is illustrated.

Referring to FIG. 15C, the result of the user's dragging manipulation 1550 provided in FIG. 15B, the TGC line 1510 has been moved outside the ultrasound image 1520 such that the TGC line 1510 no longer overlaps the ultrasound image 1520 displayed on the screen 1500. In addition, the ultrasound image 1520 has been moved to the direction opposite to the direction that the TGC line 1510 had been moved so as not to overlap the TGC line 1510. In an exemplary embodiment, as illustrated in FIGS. 15B and 15C, the detected user manipulation 1550 is indicative of dragging the TGC line 1510 to the left of the screen 1500 and thus the ultrasound image 1520 moved to the right of the screen 1500. However, one of ordinary skill in the art would recognize that the TGS line 1510 may be manipulated in right direction causing the ultrasound image 1520 to move in a left direction.

Figure 16:
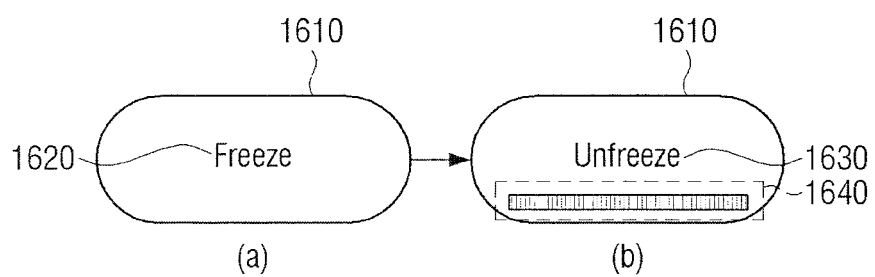
FIG. 16 illustrates an embodiment where a cine bar displayed on a still image display button according to an embodiment of the present disclosure.

FIG. 16 illustrates a cine bar displayed on a Freeze display button according to an embodiment of the present disclosure.

Referring to FIG. 16, a still image display button (e.g., a Freeze button) 1610 capable of pausing an ultrasound image being photographed in real time is illustrated. The Freeze button 1510 may be displayed on a display of the ultrasound apparatus. For example, the Freeze button 1610 includes a text indicator (e.g., "Freeze 1620" or "Unfreeze 1630") and is displayed indicating a current state based on whether the ultrasound image has been paused. In an exemplary embodiment, text indicator of Freeze 1620 is displayed within the Freeze button 1610 during an image generating state (a) and text indicator of Unfreeze 1630 is displayed on the Freeze button 1610 during a paused state (b) to release the pause state and resume photographing to generate an ultrasound image. A cine bar 1640 is displayed on a lower end within the Freeze button 1610 during the paused state (b). The cine bar 1640 is a timeline that provides an interface for searching frames of the ultrasound image from the starting point of photographing the image to the pause point. A method of manipulating the cine bar 1640 will be explained in detail later on with reference to FIGS. 17 and 18.

The Freeze button 1610 displays the text indicators "Freeze" and "Unfreeze" alternately based on a user's touch input.

Figure 17:
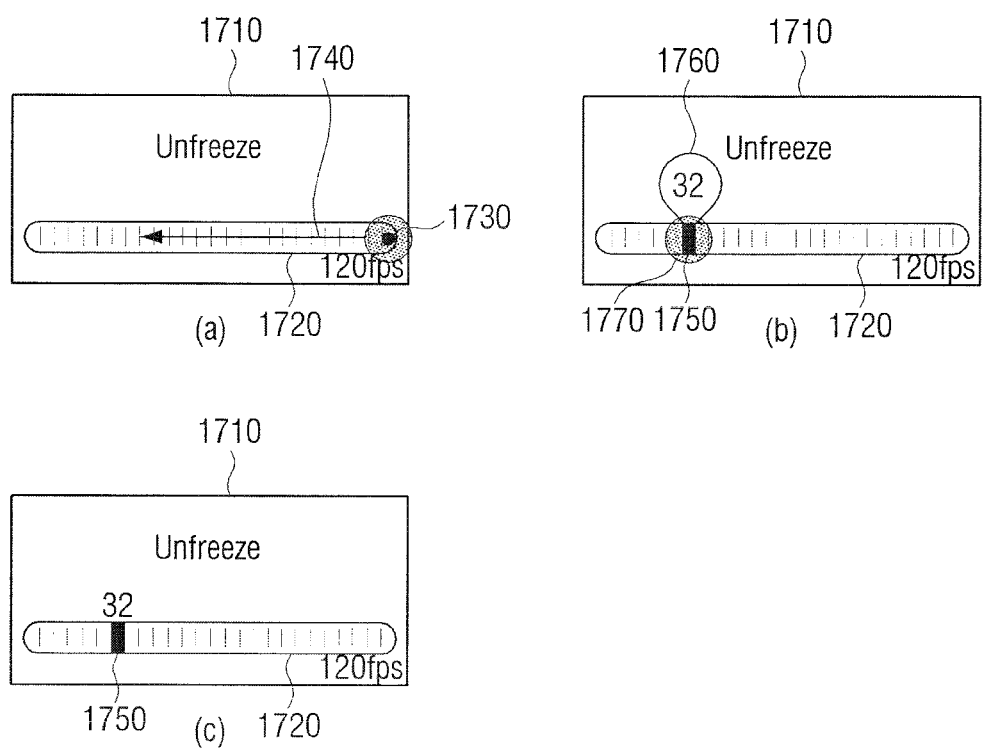
FIG. 17 is a view illustrating an embodiment of manipulating the cine bar of FIG. 16 according to an embodiment of the present disclosure.

FIG. 17 illustrates the manipulation of the cine bar of FIG. 16 according to an embodiment of the present disclosure.

Referring to FIG. 17, a first state (a) is associated with a still ultrasound image being displayed. In an exemplary embodiment, the cine bar is displayed on a lower section of the Freeze button 1710.

In order to view the ultrasound image of a desired frame, the user may input a manipulation 1740 of touching a right end 1730 of the cine bar 1720 and dragging the touch input to the left.

In a second state (b), after an input is detected associated with a user's dragging manipulation associated with the cine bar 1720 within the Freeze button 1710, an indicator 1750 is displayed indicating a position of the frame currently being displayed. While the manipulation touch 1770 of dragging continues to a second position 1750, a frame number indicator 1760 is displayed on an upper part of the second position 1750. In an exemplary embodiment, referring to FIG. 17, a number "32" may be displayed in a region associated with the second position 1750 of the manipulation input to represent the frame number of the ultrasound image.

When there is no touch detected to be associated with the cine bar 1720, the frame number indicator is modified. For example, as illustrated in FIG. 17, the frame number "32" is displayed in a small size on an upper part of the indicator 1750 to indicate the frame of the ultrasound image currently being displayed.

Figure 18:
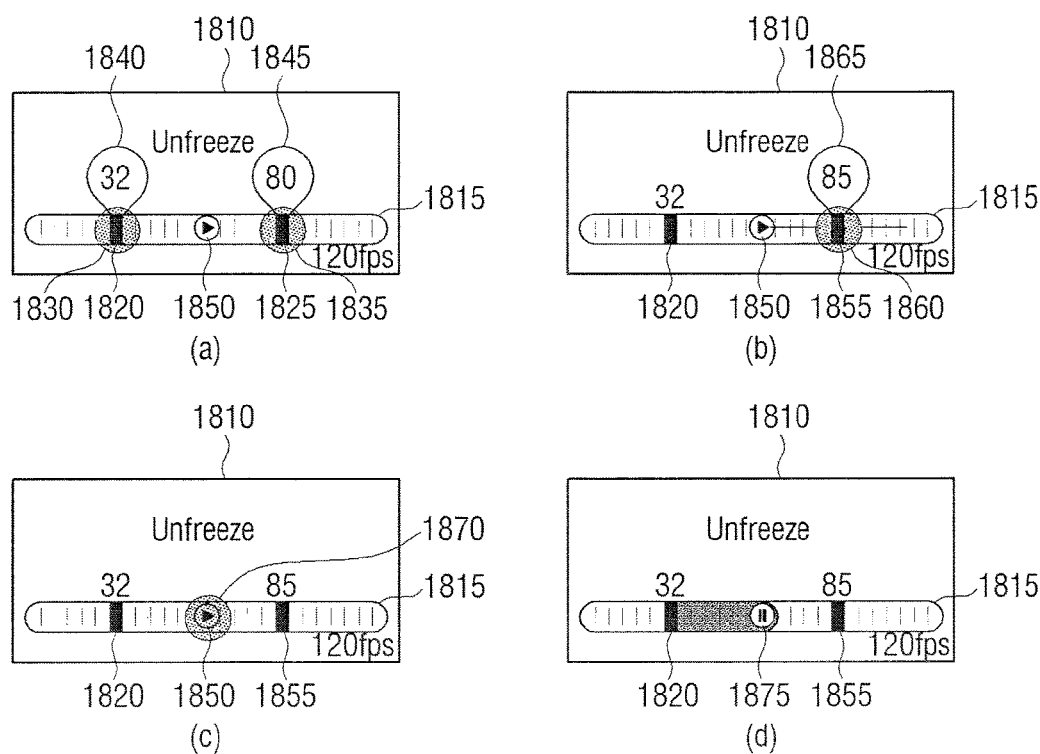
FIG. 18 is a view illustrating an embodiment of manipulating the cine bar of FIG. 16 according to an embodiment of the present disclosure.

FIG. 18 illustrates the manipulation of the cine bar of FIG. 16 according to an embodiment of the present disclosure.

Referring to FIG. 18, as illustrated at state (a), the cine bar 1815 is displayed at a lower end of the freeze button 1810. In addition, the cine bar 1815 receives an input of touches 1830, 1835 at two points. The touches 1830, 1835 at the two points may be touched one at a time sequentially, or at the same time. Two indicators 1820, 1825 may be displayed on the cine bar 1815 corresponding to the two touched points 1830, 1835. In addition, at an upper part of each of the touched indicator 1820, 1825, frame indicators 1840 and 1845 (e.g., "32" and "88") representing the order of the frames corresponding to the positions being touched are displayed in large sizes. In addition, between the two indicators 1820, 1825, a reproduce button 1850 is further displayed.

As illustrated in state (b), after a touch input is received associated with one 1855 of the two indicators 1820, 1855 displayed and a manipulation 1860 of the one indicator 1855 is detected along the cine bar 1815, the indicator 1855 associated with an initial touch may be moved to the second manipulation point 1850 corresponding to a different frame. In an exemplary embodiment, the indicator 1855 associated with the ultrasound image of frame 80 illustrated in state (a) was moved to a second location 1860 indicating the ultrasound image of frame 85 illustrated in state (b).

After confirming a section of ultrasound image to reproduce, the user may input a manipulation 1870 associated with touching a reproduce button 1850 displayed between the two indicators 1820, 1855 on the cine bar 1815 illustrated in state (c).

Referring to FIG. 18, the reproduce button 1850 illustrated in state (c) is modified to a freeze button 1875 illustrated in state (d) when a touch input manipulation is detected associated with the reproduce button 1850. In an exemplary embodiment, the ultrasound image is reproduced from the frame where the left indicator 1820 is located to the frame where the right indicator 1855 is located at a speed of 120 frames per second (fps). While the ultrasound image is being reproduced, a color of the position corresponding to the reproduced frame may be changed on the cine bar 1815 and displayed in order to indicate the degree of reproduction.

The freeze button 1875 and reproduce button 1850 may be toggled and displayed every time a user's touch input is detected.

Figure 19A:
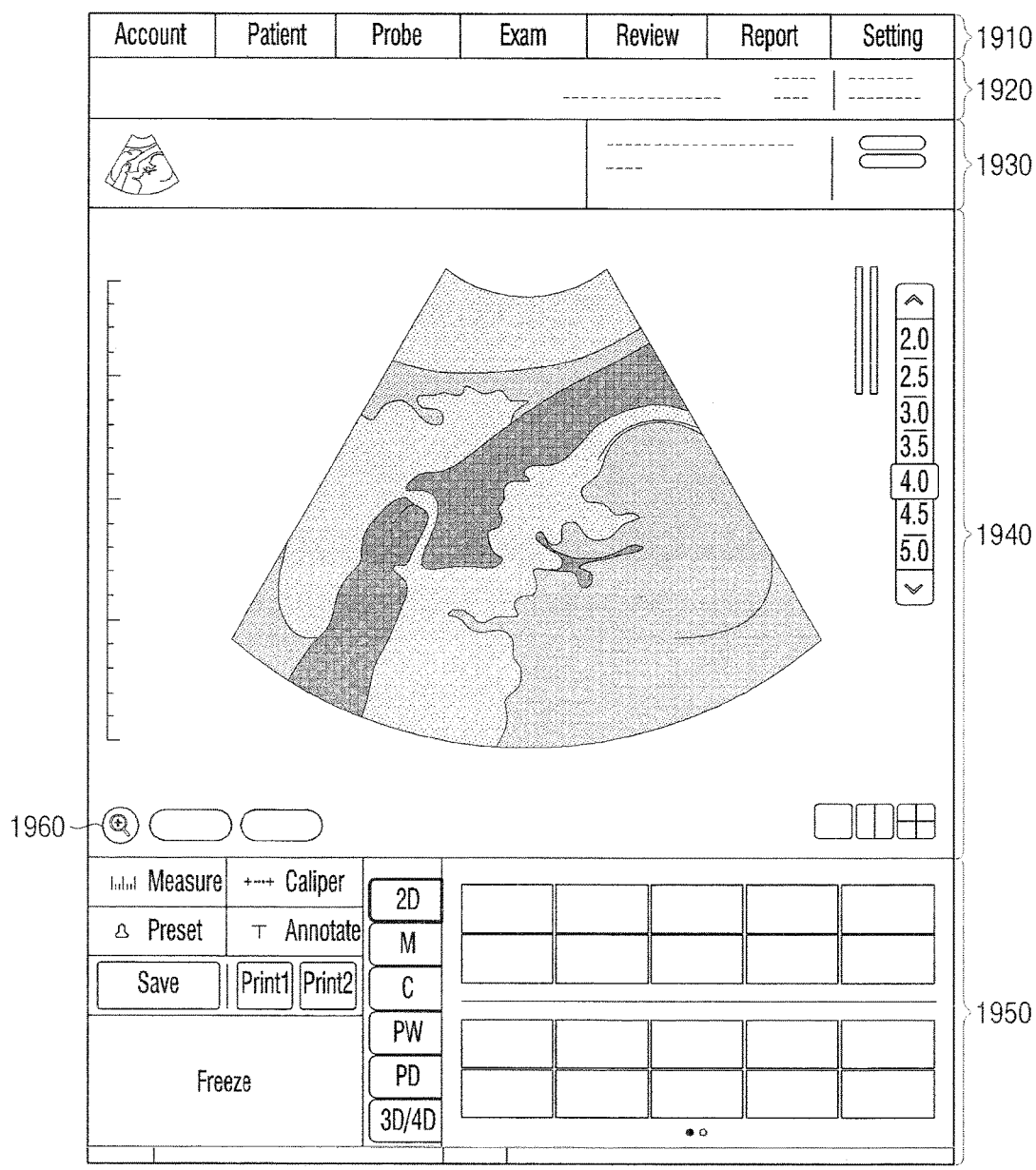
FIGS. 19A and 19B are views illustrating an embodiment where a layout of a screen is automatically changed by execution of a certain function according to an embodiment of the present disclosure.
Figure 19B:
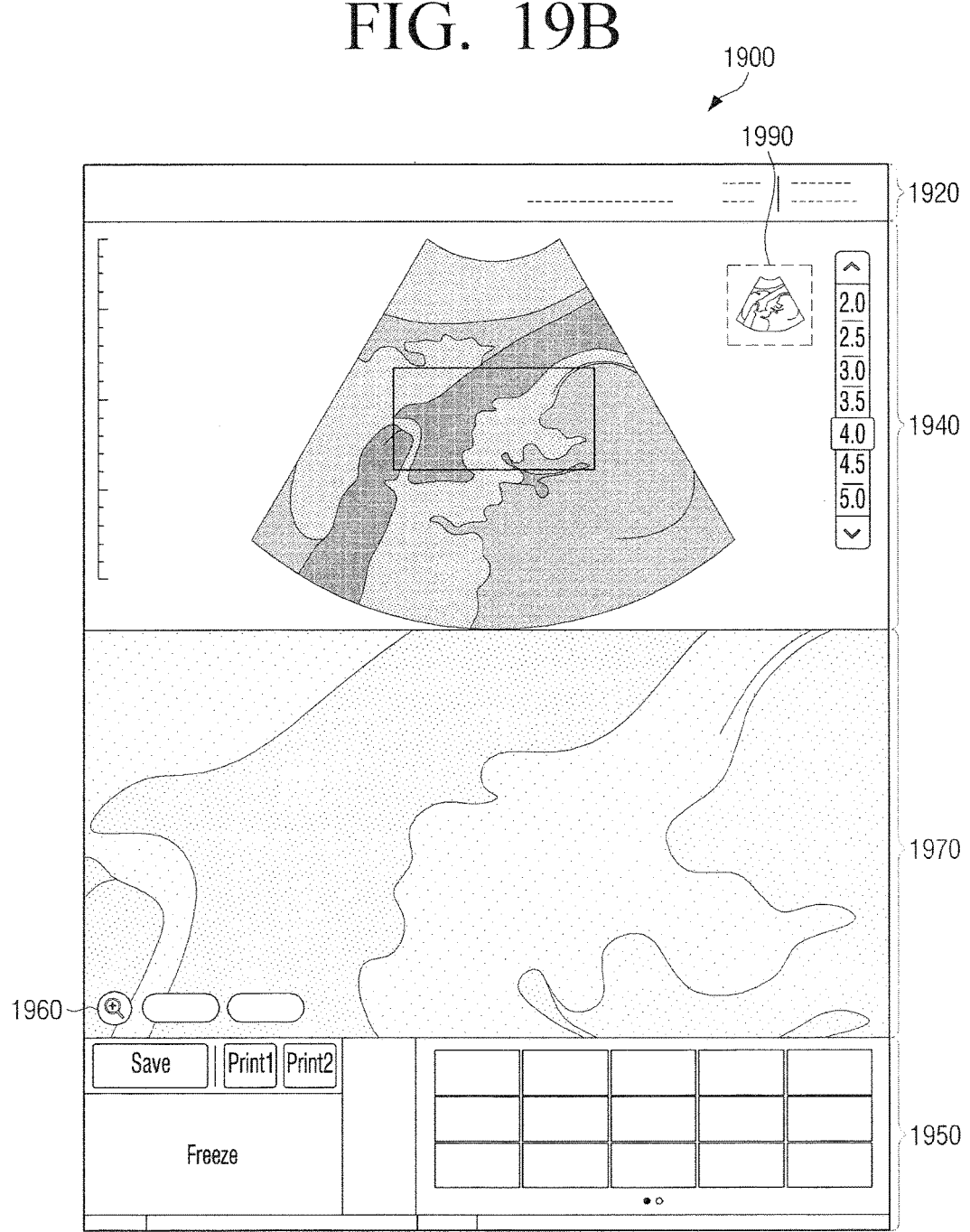

FIGS. 19A and 19B are views illustrating an embodiment of the present disclosure where a layout of a screen is automatically changed by execution of a certain function.

Referring to FIG. 19A, the screen 1900 may be divided into five regions 1910, 1920, 1930, 1940, 1950 divided vertically. In addition, on the image region 1940 where the ultrasound image is displayed, an expansion button 1960 for executing an expanding function is displayed.

The user may touch the expansion button 1960 to expand or zoom a portion of the ultrasound image.

Referring to FIG. 19B, a region 1970 where an expanded image associated with the interaction with the expansion button 1960 is further displayed on the screen 1900. In an exemplary embodiment, regions 1910, 1930 that contain options and information illustrated in FIG. 19A may be unnecessary in the expanded view are not displayed in FIG. 19B. In addition, the region 1950 in the lowermost part of the screen 1900 is displayed in a reduced size. Accordingly, a space for displaying the expanded image is obtained.

Figure 20A:
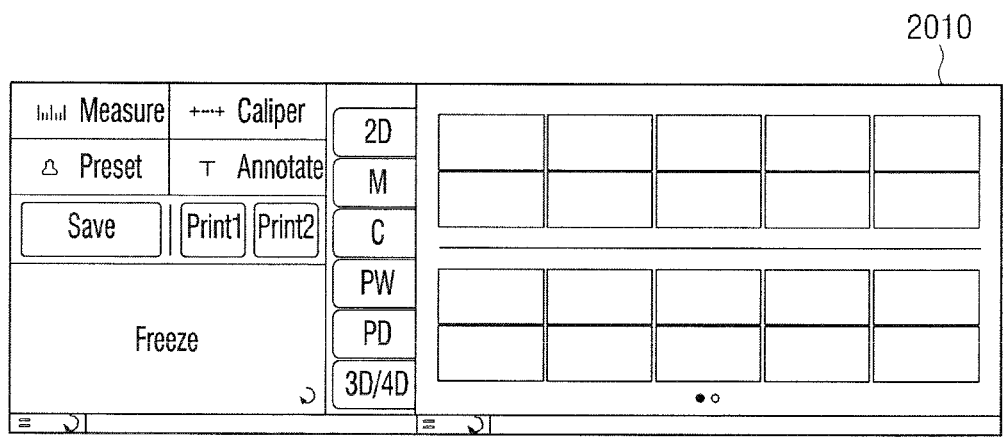
FIGS. 20A and 20B are views illustrating an embodiment where a layout of a screen is automatically changed by execution of a certain function according to an embodiment of the present disclosure.
Figure 20B:
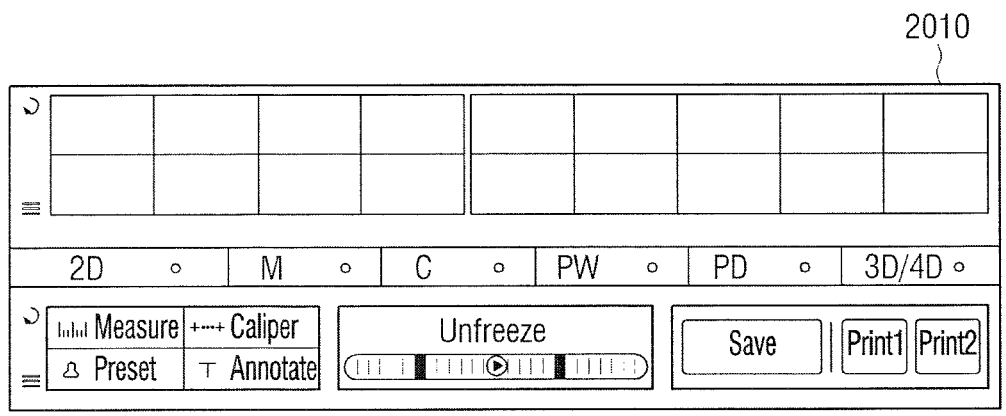

FIGS. 20A and 20B illustrates where a layout of a screen is automatically changed by execution of a certain function according to an embodiment of the present disclosure.

Referring to FIG. 20A, a view illustrating a region 2010 where a quick menu and sub menu of the basic layout is displayed. In an exemplary embodiment, the user may touch a certain button of the sub menu and execute an application within screen 1900 illustrated in FIGS. 19A and 19B.

Referring to FIG. 20B, a state where an arrangement of the objects in the quick menu and sub menu of region 2010 are changed thereby modifying the arrangement of the quick menu horizontally at a lowermost part is illustrated.

Touch Interaction for Moving Expanded Region

FIGS. 21A to 21D are views illustrating four manipulations associated with changing a state of display when executing a function of expanding an image.

Figure 21A:
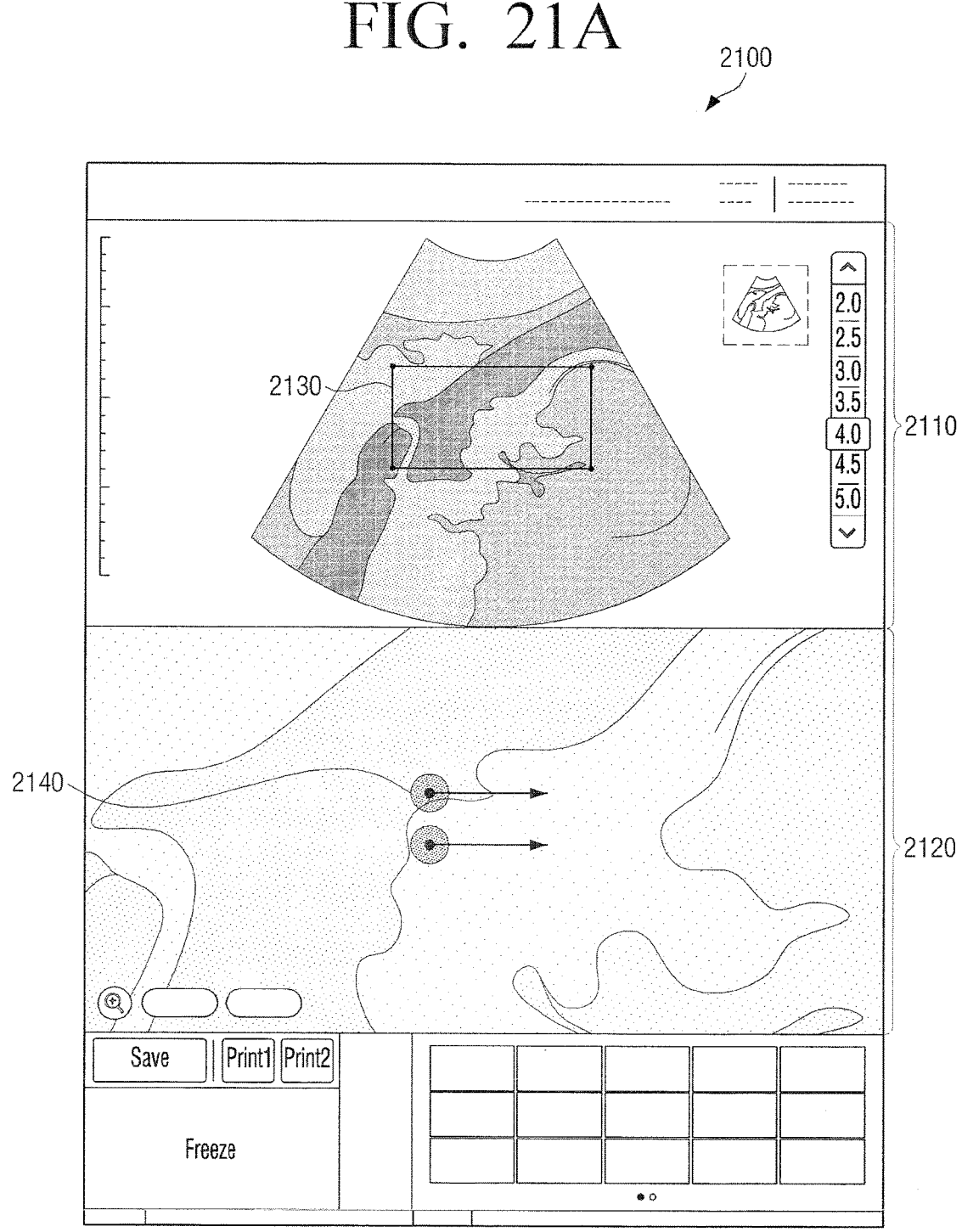
FIGS. 21A to 21D are views illustrating four types of manipulations of changing a displaying state when a close-up view function is executed according to an embodiment of the present disclosure.

Referring to FIG. 21A, on the screen 2100 where the expanding function has been activated, an image region 2110 is displayed at an upper portion, and an expanded region 2120 is displayed on a lower portion. In an exemplary embodiment, a view of the entirety of the photographed ultrasound image and a guide box 2130 for indicating a region to be expanded are displayed within the image region 2110.

Touch inputs 2140 associated with a manipulation of panning two points touched while viewing an expanded image may be received with the expanded region 2120 where the manipulation indicate that a part of the image region 2110 is to be expanded and viewed within the expanded region 2120. In an exemplary embodiment, the ultrasound image associated with the image region 2110 may be moved under the fixed guide box 2130 such that the touch input 2140 corresponds to the movement of the expanded image.

Figure 21B:
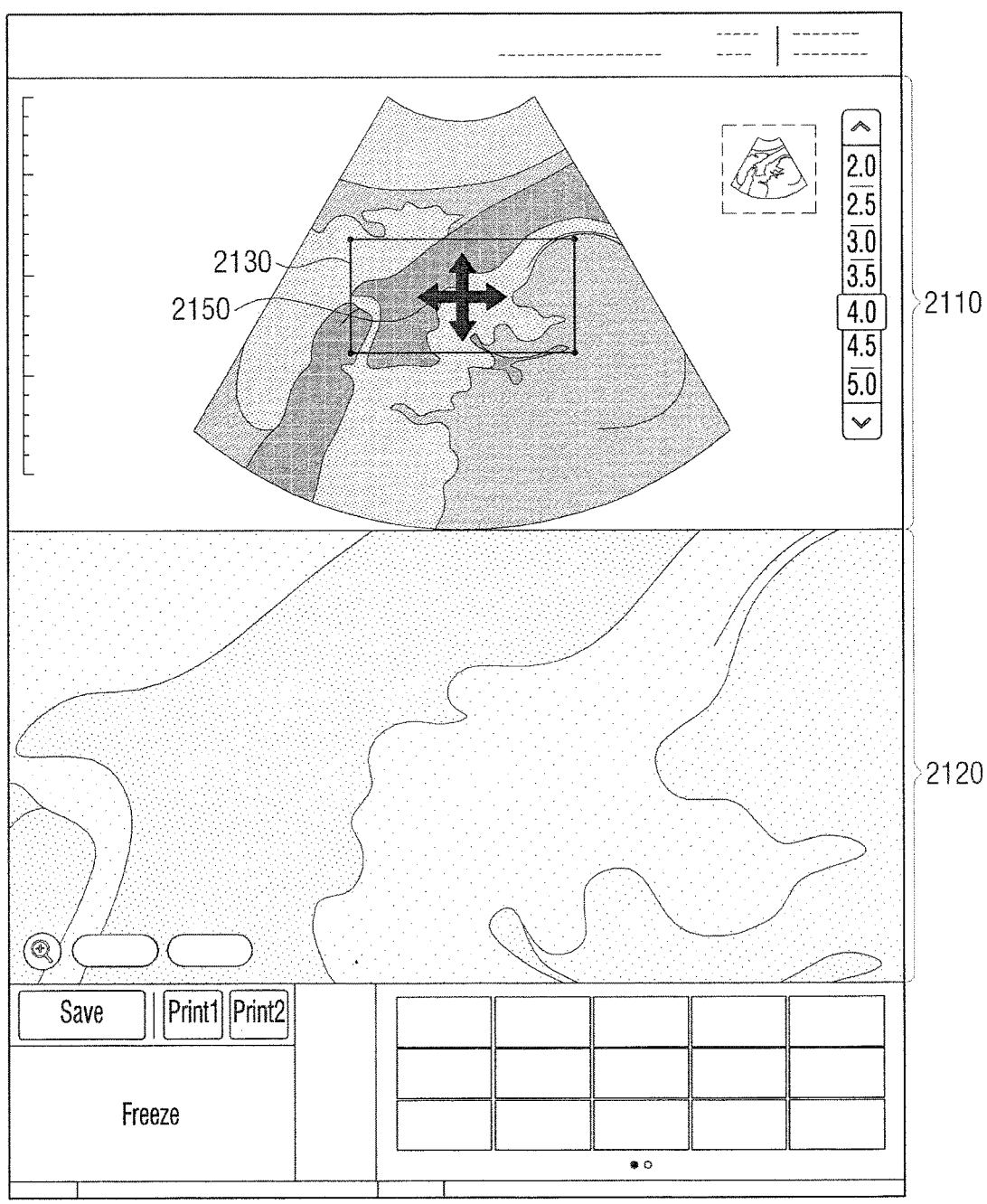

Referring to FIG. 21B, the user may input a touch input manipulation associated with touching and panning within the guide box 2130 in the image region 2110 in order move the part of the image to be expanded and viewed within the expanded region 2120. More specifically, when the user inputs a panning touch 2150, the guide box 2130 may be moved over the ultrasound image thereby moving the portion of the ultrasound image to be expanded and viewed within the expanded region 2120.

Figure 21C:
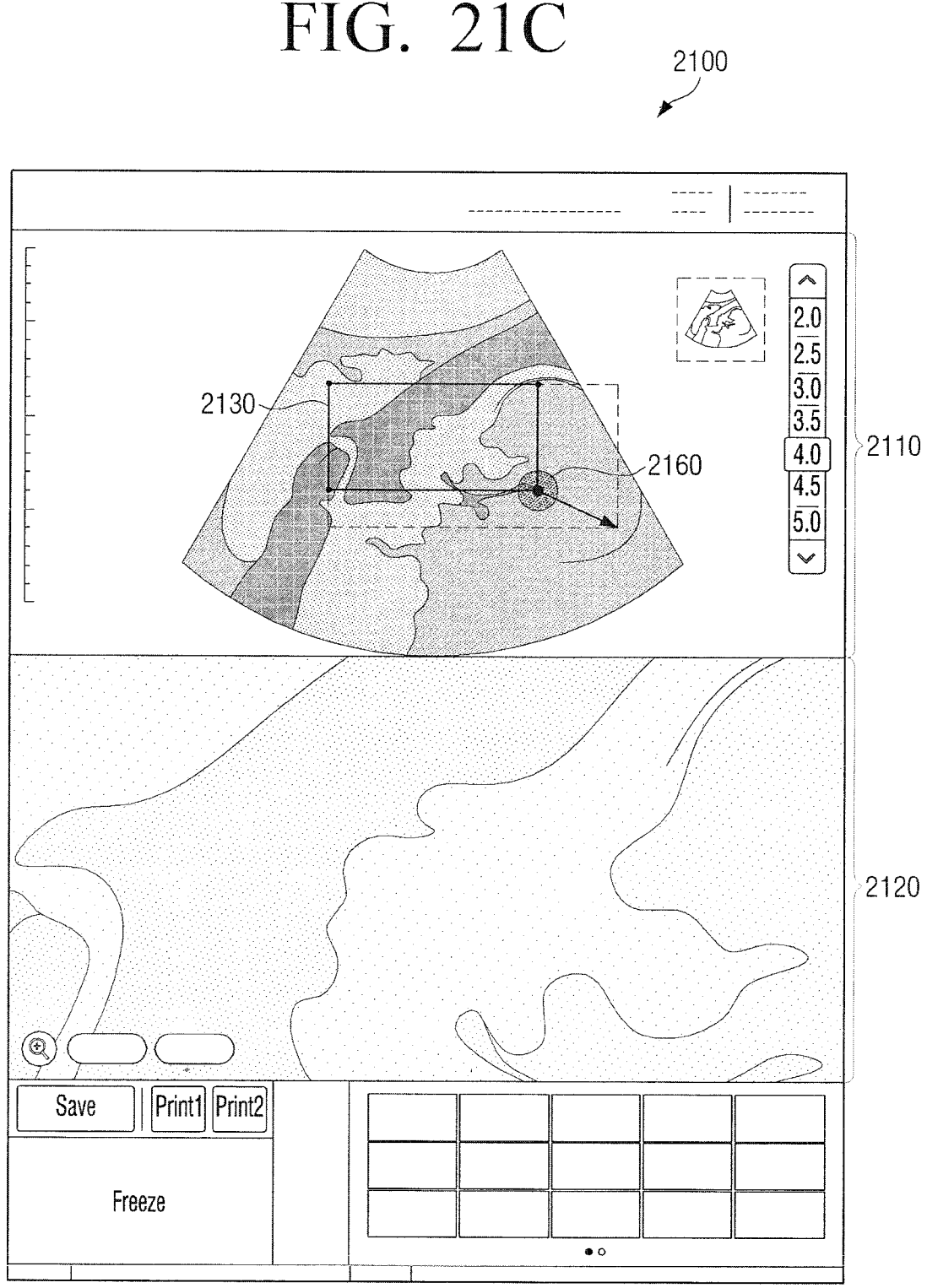

Referring to FIG. 21C, a size of the guide box 2130 may be modified by a manipulation 2160 of touching and dragging one of four vertices of the guide box 2130 thereby expanding the size of the image displayed in the expanded region 2120 at a predetermined rate.

Figure 21D:
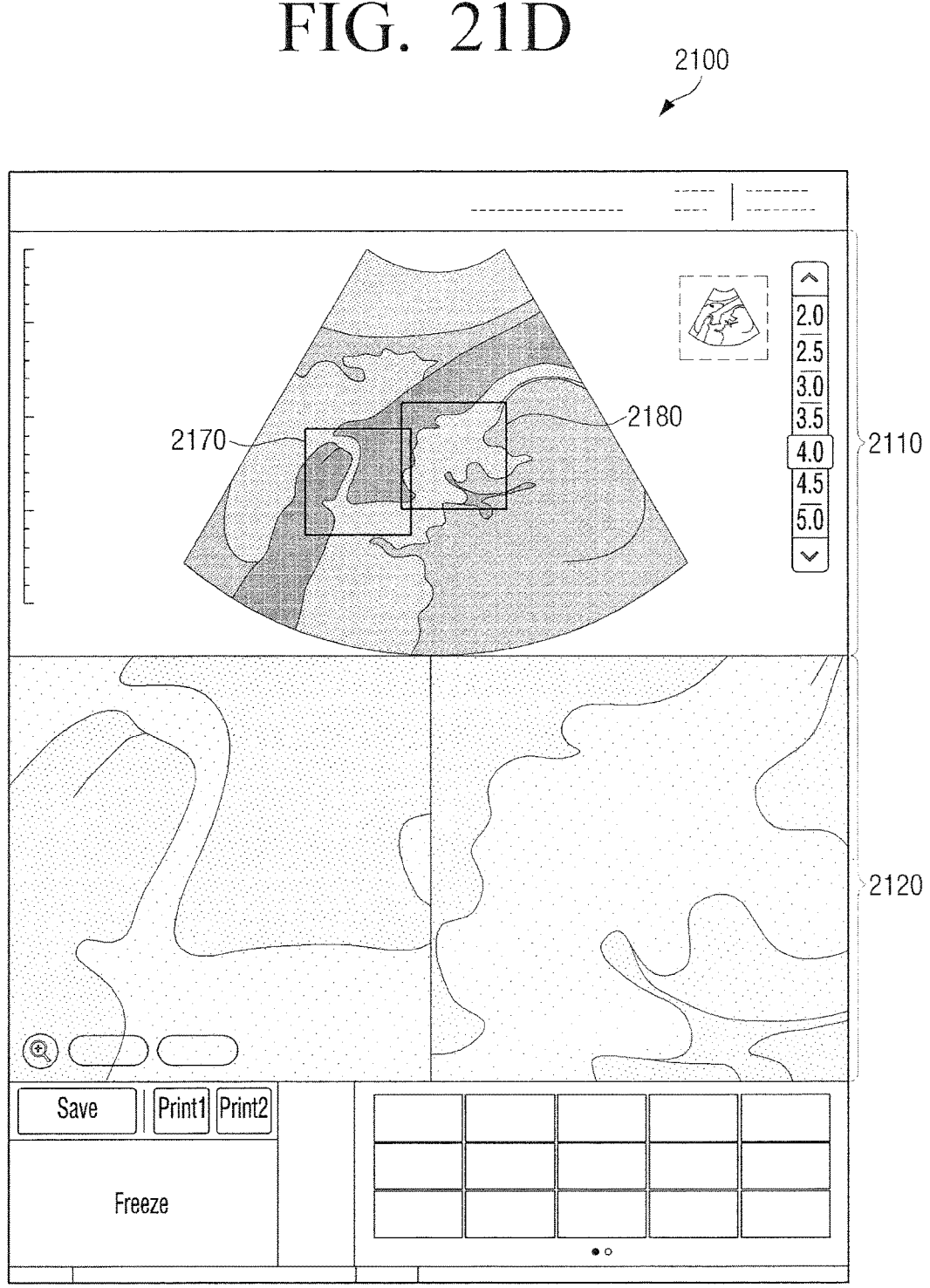

Referring to FIG. 21D, a plurality of guide boxes 2170, 2180 are displayed on the image region 2110 and an expanded region 2120 where the expanded image corresponding to each guide box 2170, 2180 is divided is displayed within the expanded region 2120 of screen 2100.

Touch Interaction for Setting Focusing and Depth

Figure 22:
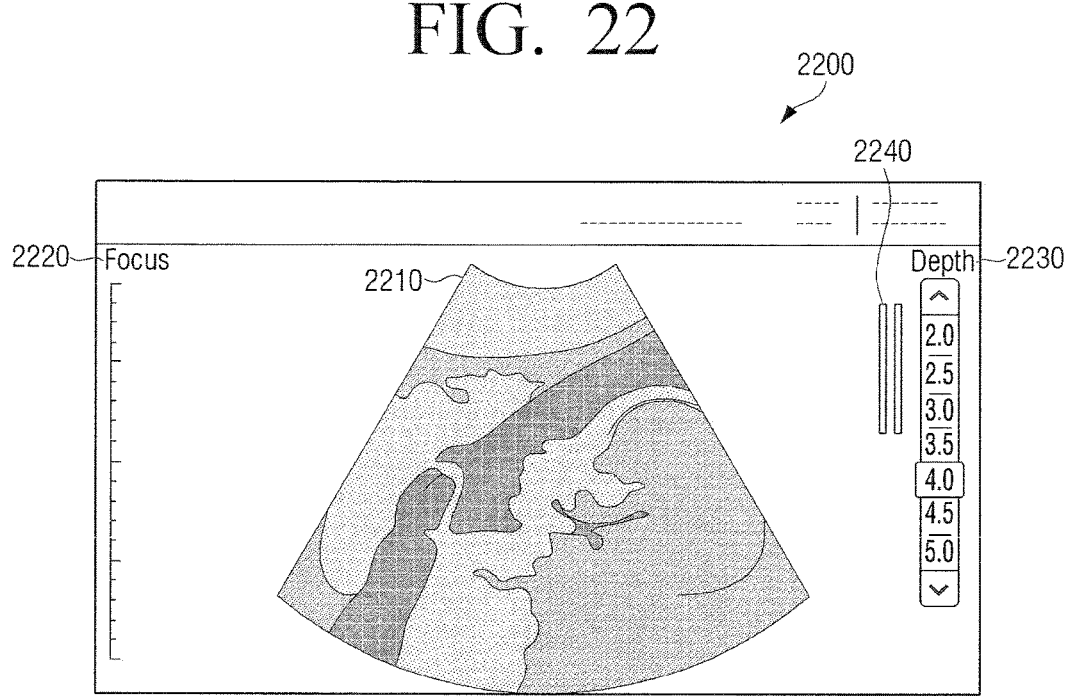
FIG. 22 is a view illustrating a configuration of an image display region according to an embodiment of the present disclosure.

FIG. 22 is a view illustrating a configuration of an image region according to an embodiment of the present disclosure.

Referring to FIG. 22, the image region 2200 includes an ultrasound image 2210, a focus adjuster 2220, a depth adjuster 2230, and a gamma/brightness adjuster 2240.

A region where the ultrasound image 2210 is displayed may be divided into a plurality of depth regions according to depth. In other words, regions of bands corresponding to a same depth of an examination object may be classified into one depth region.

The focus adjuster 2220 displays a depth of a current image that is in focus. More specifically, the focus adjuster 2220 may display a depth in which to focus ultrasound waves being emitted may be configured. A plurality of focuses may be set for different depths where the different focus values affect a resolution of an image corresponding to a depth that is in focus.

The depth adjuster 2230 displays a depth of an ultrasound image currently being displayed. More specifically, the depth adjuster 2230 may display a depth of an ultrasound image to be displayed based on a reflected wave received.

The gamma/brightness adjuster 2240 provides an interface for setting at least one of a gamma, a brightness, and a contrast associated with an image to be output so that the user may identify the image better.

Figure 23:
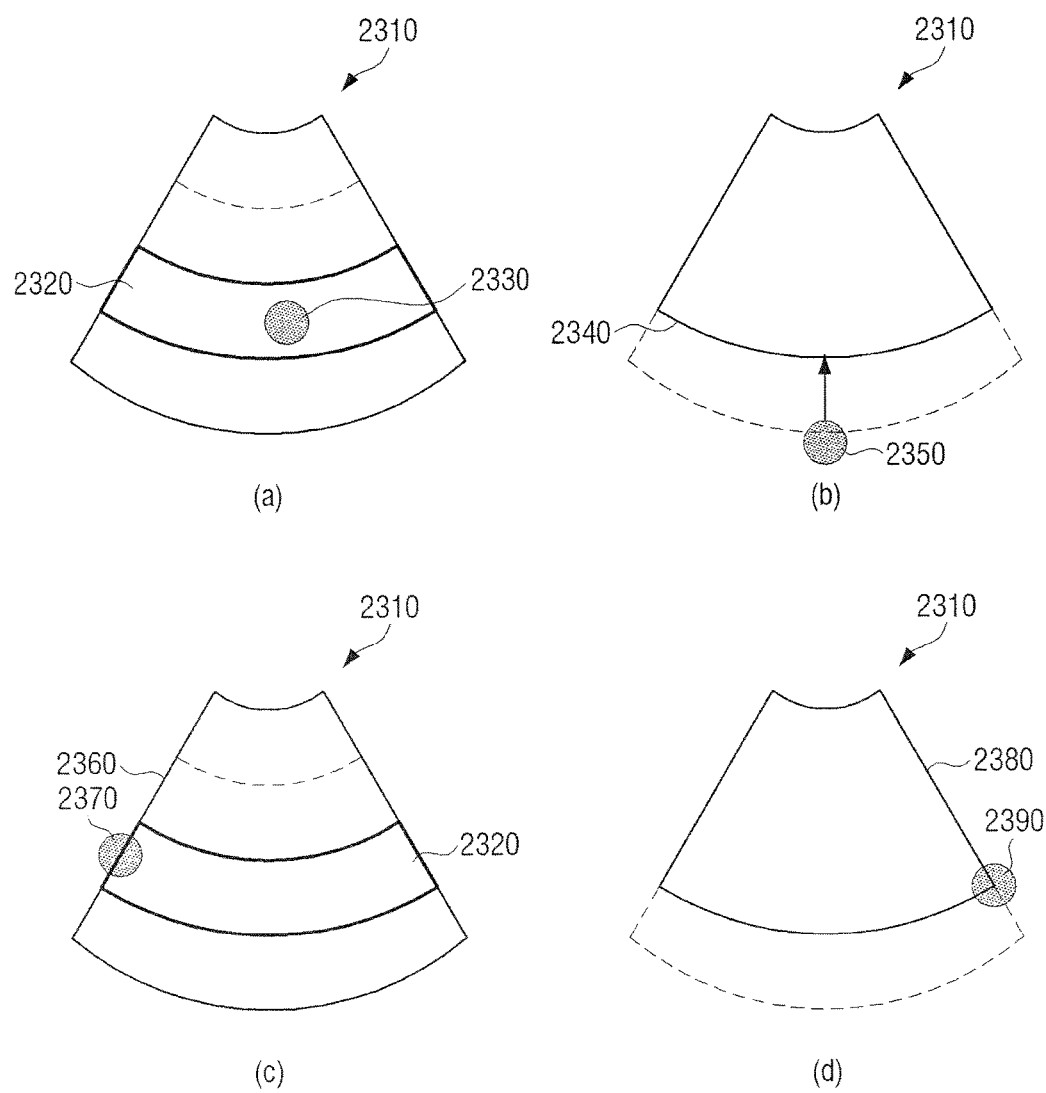
FIG. 23 is a view illustrating a manipulation of setting a focus or depth of an ultrasound image according to an embodiment of the present disclosure.

FIG. 23 illustrates a manipulation of setting associated with a focus or a depth of an ultrasound image according to an embodiment of the present disclosure.

Referring to FIG. 23, state (a) illustrates a manipulation 2330 of a user touching inside an ultrasound image 2310. A depth 2320 corresponding to a position touched by the user may be made to be in focus.

State (b) illustrates a manipulation 2350 of a user dragging an end corner of depth direction of an ultrasound image 2310. A depth of the ultrasound image 2310 being displayed may be set to the dragged position.

State (c) illustrates a manipulation 2370 of the user touching one corner 2360 of among both corner regions 2320 parallel to the depth direction of the ultrasound image 2310. A focus may be set on a depth 2320 corresponding to the touched position.

State (d) illustrates a manipulation 2390 of the user touching the other corner 2380 of among the both corner regions parallel to the depth direction of the ultrasound image 2310. A depth of the ultrasound image 2310 to be displayed may be set to the depth corresponding to the touched position.

Figure 24:
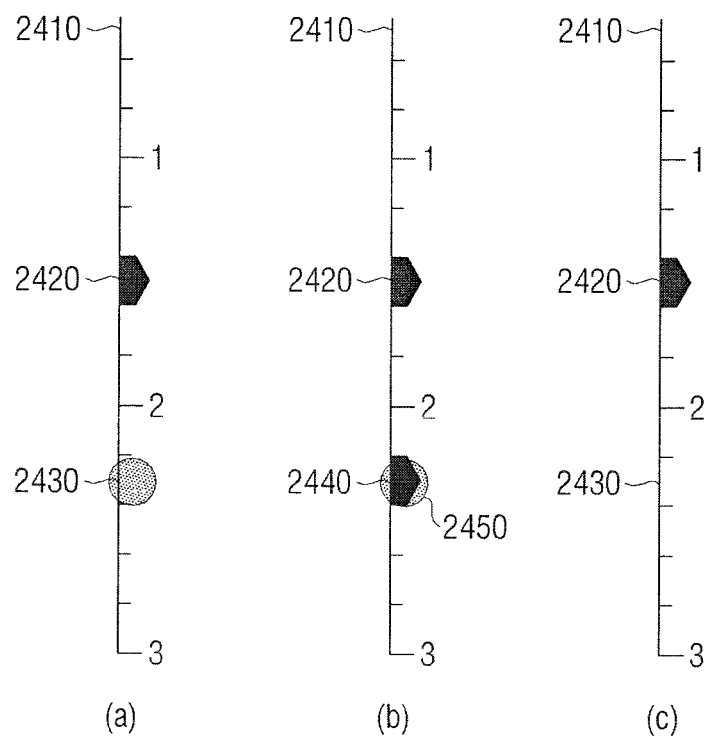
FIG. 24 is a view illustrating a manipulation of setting a focus of an ultrasound image according to an embodiment of the present disclosure.

FIG. 24 illustrates a manipulation of setting a focus of an ultrasound image according to another embodiment of the present disclosure.

Referring to FIG. 24, state (a) illustrates an indicator 2420 that indicates a depth that has been set to be in focus automatically when executing the focus adjuster 2410 for the first time. In addition, the user inputs a touch manipulation 2430 associated with tapping a position corresponding to a depth to be made to be in focus in the focus adjuster 2410.

State (b) illustrates an additional indicator 2440 is displayed on a point where the touch input of the focus adjuster 2410 has been detected. A depth corresponding to the position where the user's touch has been detected may be set to be in focus. In addition, the user inputs a touch manipulation 2450 associated with tapping the displayed indicator 2440.

State (c) illustrates a state where the indicator 2440 of the tab manipulation of the focus adjuster 2410 is not displayed at position 2430. In this case, the focus setting corresponding to the disappeared indicator 2440 is deleted.

Figure 25:
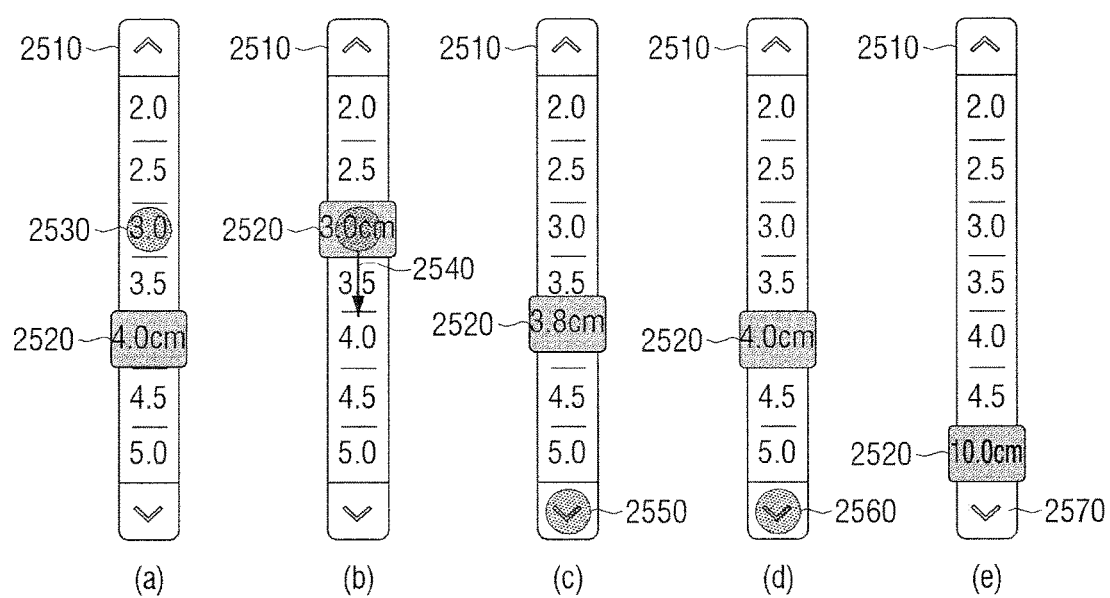
FIG. 25 is a view illustrating a manipulation of setting a depth of an ultrasound image according to an embodiment of the present disclosure.

FIG. 25 illustrates a manipulation of setting a depth of an ultrasound image according to another embodiment of the present disclosure.

Referring to FIG. 25, at state (a), the depth adjuster 2510 together with an indicator 2520 may be manipulated to indicate a depth of a current ultrasound image. A number indicating the depth is displayed inside the indicator 2520. In an exemplary embodiment, the user inputs a touch manipulation 2530 associated with tapping the number of a desired depth.

State (b) illustrates a state where the indicator 2520 has moved to a position where a touch of the depth adjuster 2510 was detected and a number indicating a depth is highlighted and displayed inside the indicator 2520. A depth of the ultrasound image to be displayed is set to a depth corresponding to a position where the user's tap manipulation has been detected. In an exemplary embodiment, the user inputs a manipulation 2540 of touching and dragging the indicator 2520.

State (c) illustrates a state where the indicator 2520 moves continuously according to the user's dragging manipulation and the number displayed inside the indicator 2520 is changed to a decimal number. By changing the number inside the indicator 2520 to a decimal number, fine control the depth of the ultrasound image to be displayed may be achieved. The user may input a touch manipulation 2550 of tapping one of up/down buttons arranged at both sides of the depth adjuster 2510.

State (d) illustrates a state where the indicator 2520 has moved to a position corresponding to a depth of predetermined units associated with the user's manipulation of touching the down button to increase the depth of the ultrasound image to be displayed. In an exemplary embodiment, as illustrated in state (d) of FIG. 25, the minimum unit of depth that may be changed by the up/down button is 0.5 cm. The user may repeatedly input the touch manipulation 2560 of tapping the down button in order to set the depth to the maximum depth.

State (e) illustrates a state where the indicator 2520 has reached the maximum depth. In an exemplary embodiment, the color of the down button 2570 may be shaded darker in order to visually indicate that the maximum depth has been reached thereby deactivating the down button 2570.

Figure 26:
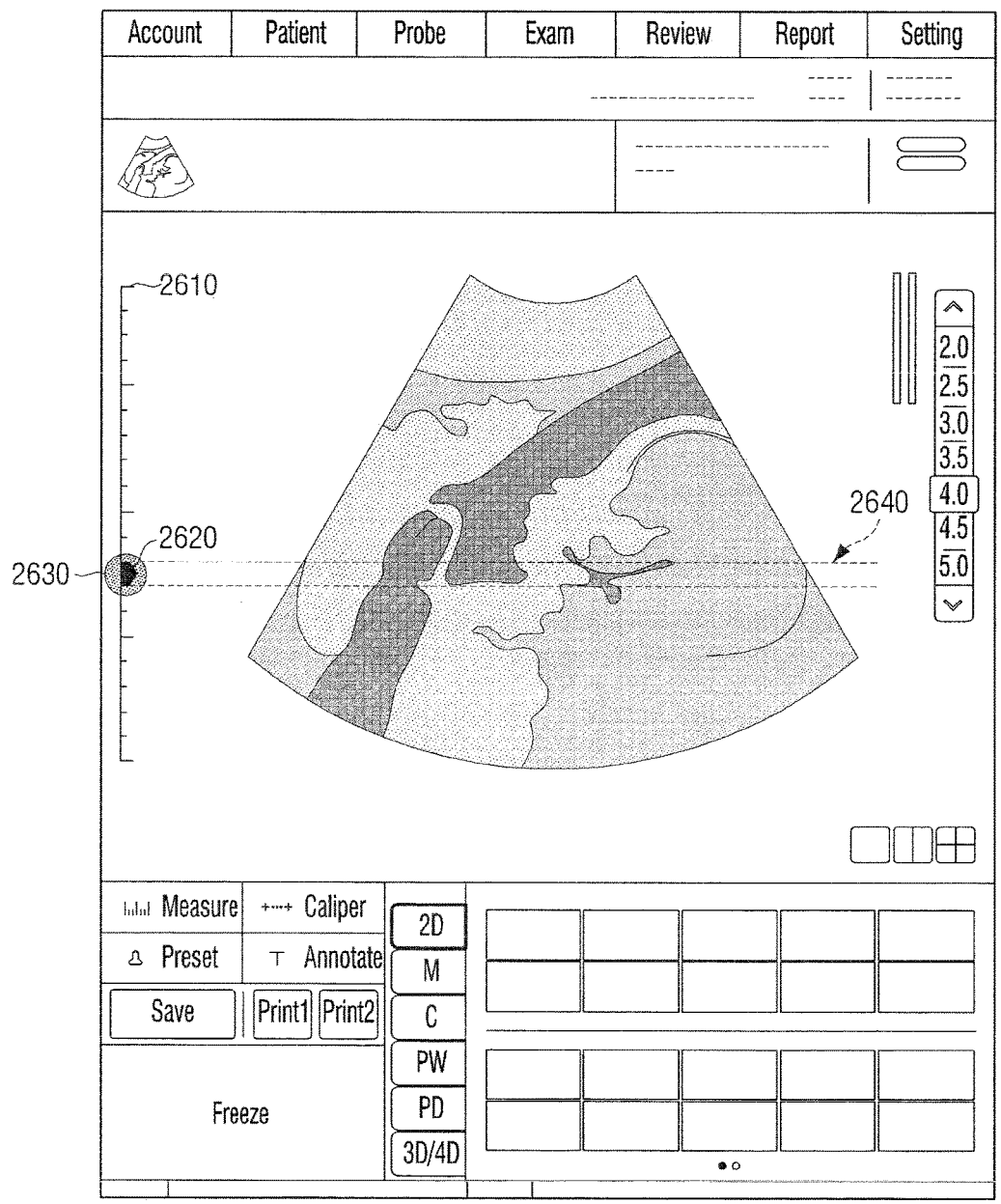
FIG. 26 is a view illustrating an example of a screen where the manipulation of FIG. 24 has been applied according to an embodiment of the present disclosure.

FIG. 26 is a view illustrating an example of a screen where the manipulation of FIG. 24 has been applied.

Referring to FIG. 26, in the focus adjuster 2610, the user may perform a manipulation 2630 by touching a position corresponding to a depth of the ultrasound image desired to be in focus on screen 2600. By the user's touch manipulation, an additional indicator 2620 may be displayed in the focus adjuster 2610 together with a guideline 2640 consisting of two traverse lines starting from the indicator 2620.

The guideline 2640 is displayed to overlap the ultrasound image thereby enabling the user to visually identify which part of the ultrasound image the depth to be made to be in focus by the user's touch corresponds to.

FIGS. 27A to 27D are views illustrating an example of a screen where the manipulation of FIG. 25 has been applied.

Figure 27A:
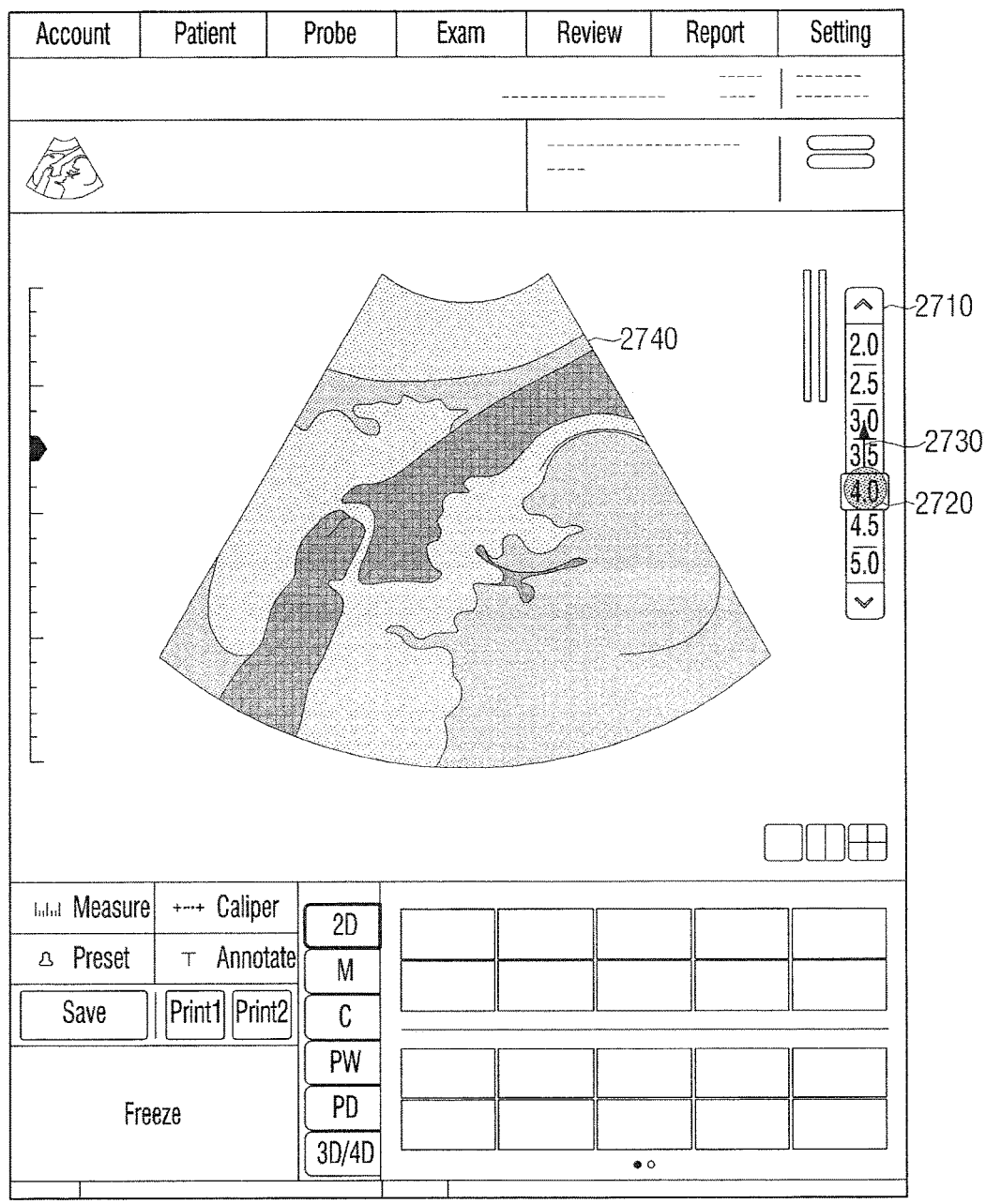
FIGS. 27A to 27D are views illustrating an example of a screen where the manipulation of FIG. 25 has been applied according to an embodiment of the present disclosure.

Referring to FIG. 27A, the user may input a manipulation 2730 of touching the indicator 2720 displayed on the depth adjuster 2710 at screen 2700 and dragging it upwards to modify the depth of focus associated with the ultrasound image 2740.

Figure 27B:
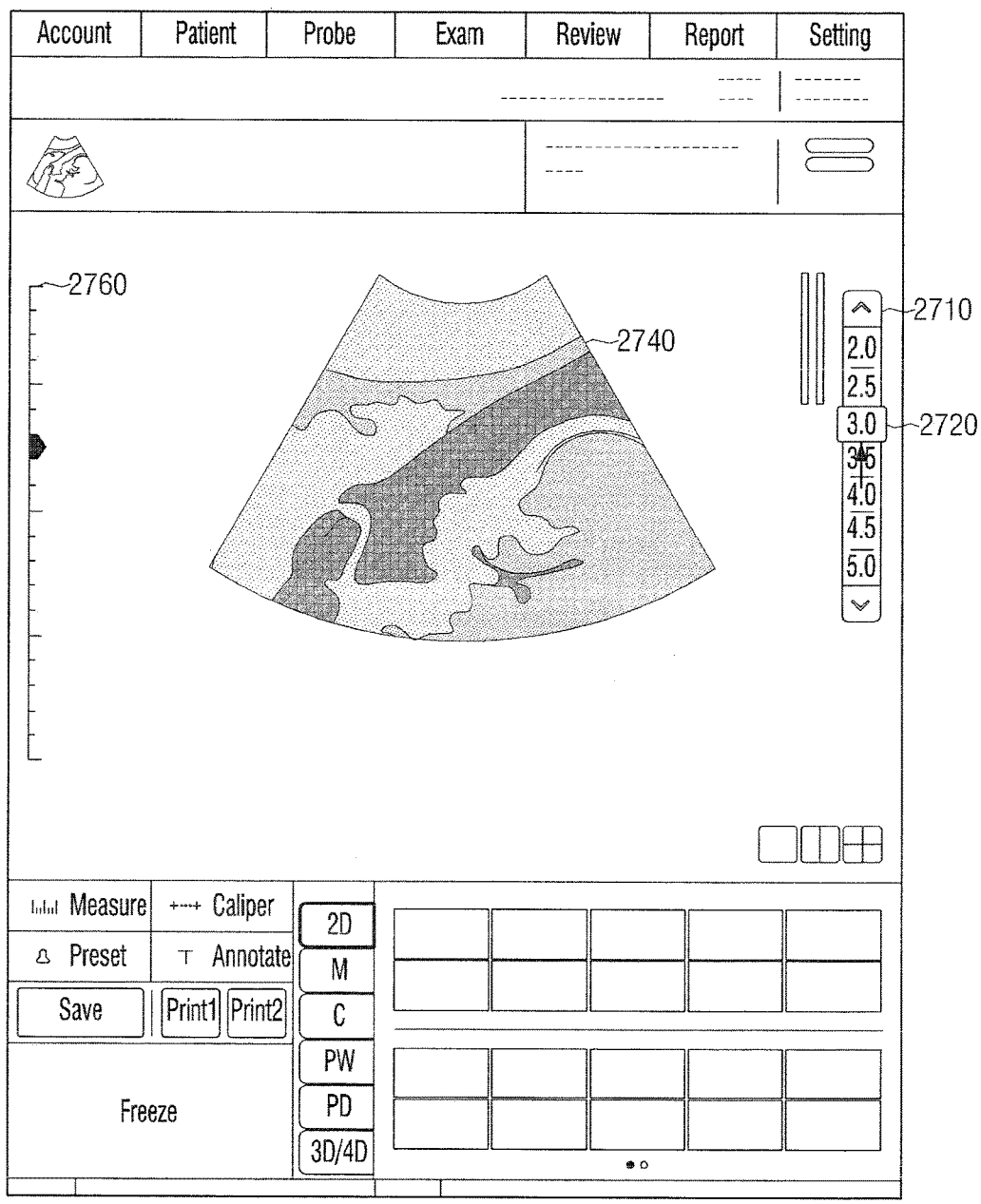

Referring to FIG. 27B, a depth of the ultrasound image 2740 to be displayed changes according to a position in which the indicator 2720 has been dragged within the depth adjuster 2710. For example, the ultrasound image 2740 is displayed to reflect any changed depth. In an exemplary embodiment, the unit of gradations of the focus adjuster 2760 may also be changed to correspond to the changed depth.

Figure 27C:
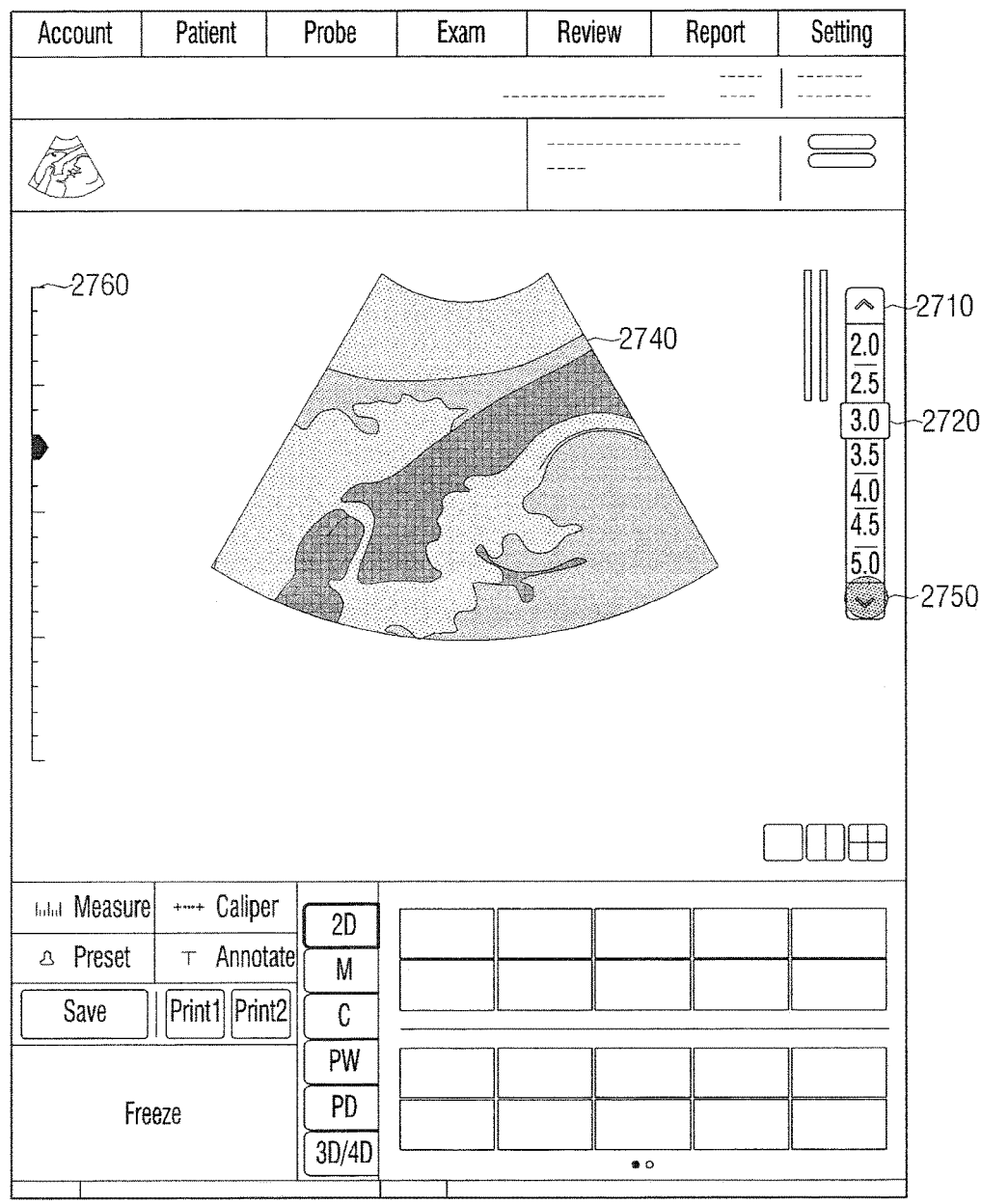

Referring to FIG. 27C, the user may input a manipulation 2750 associated with tapping the down button of the depth adjuster 2710 may cause the position of the indicator 2720 to be modified.

Figure 27D:
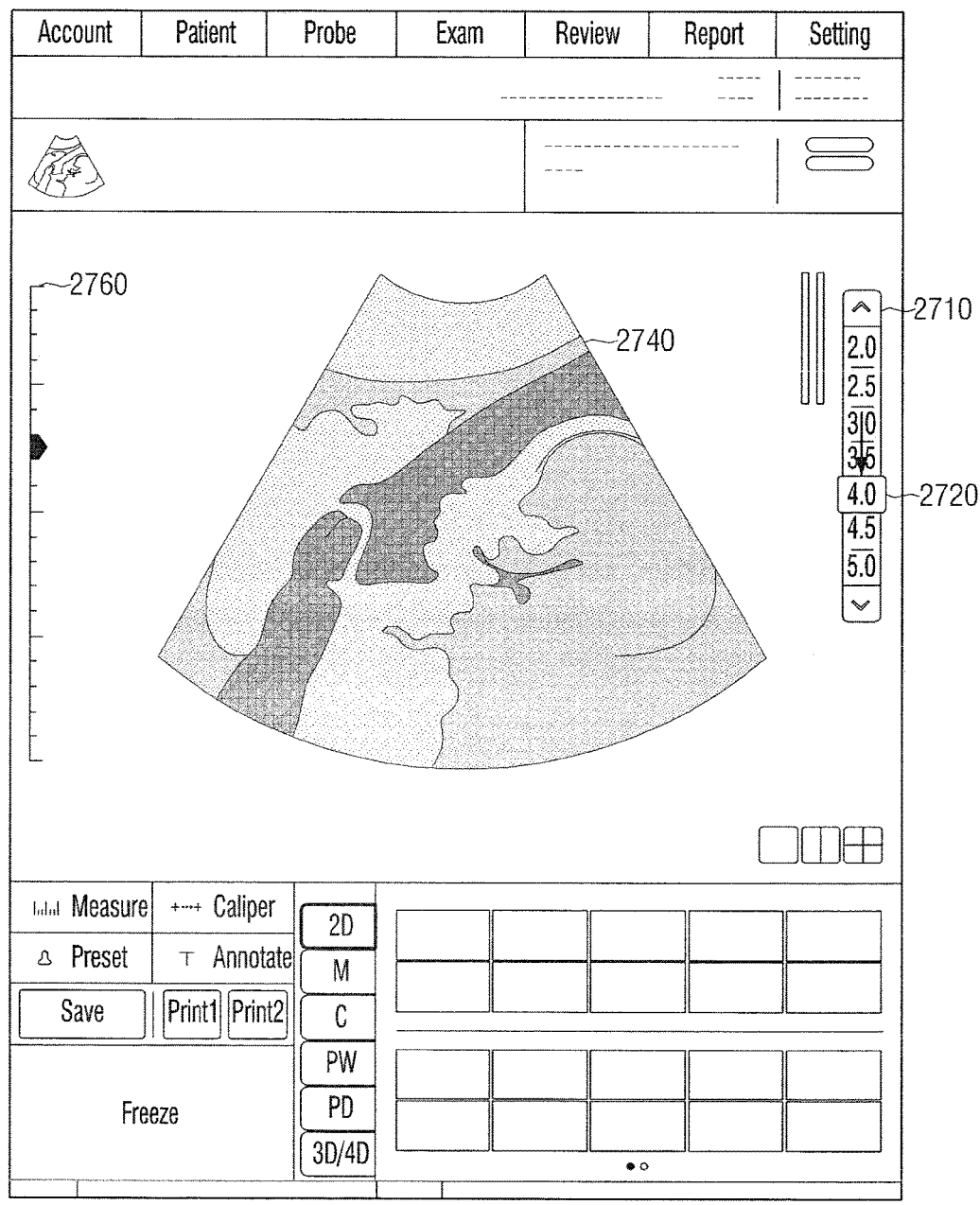

Referring to FIG. 27D, the depth may be changed based on the number of times a manipulation 2750 of tapping the down button is detected may be reflected in predetermined units where the indicator 2720 indicates the resulting depth. In addition, the ultrasound image 2740 is modified to reflect the changed depth.

Touch Interaction for Setting TGC

Figure 28A:
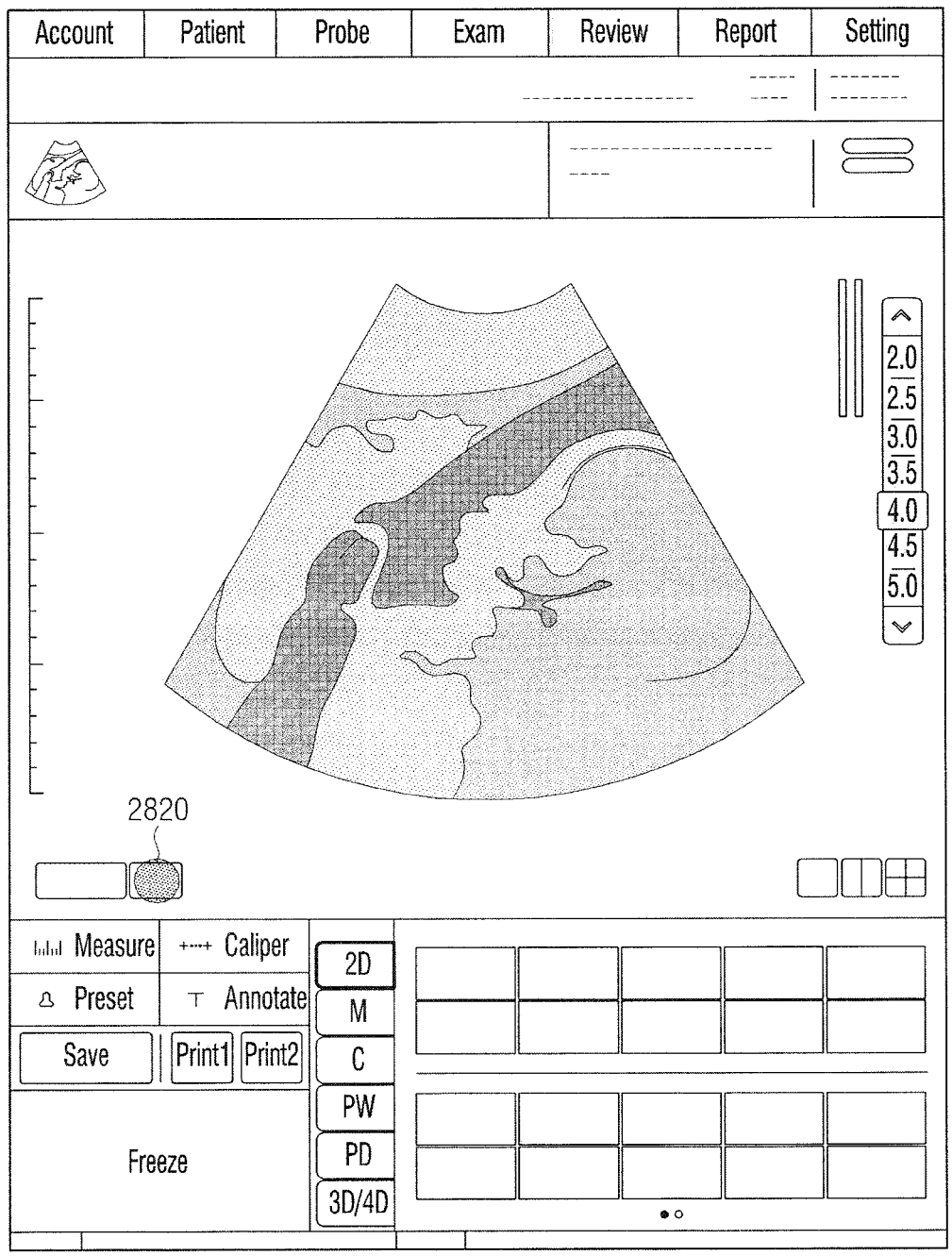
FIGS. 28A to 28C are views illustrating a manipulation of setting a TGC according to an embodiment of the present disclosure.
Figure 28B:
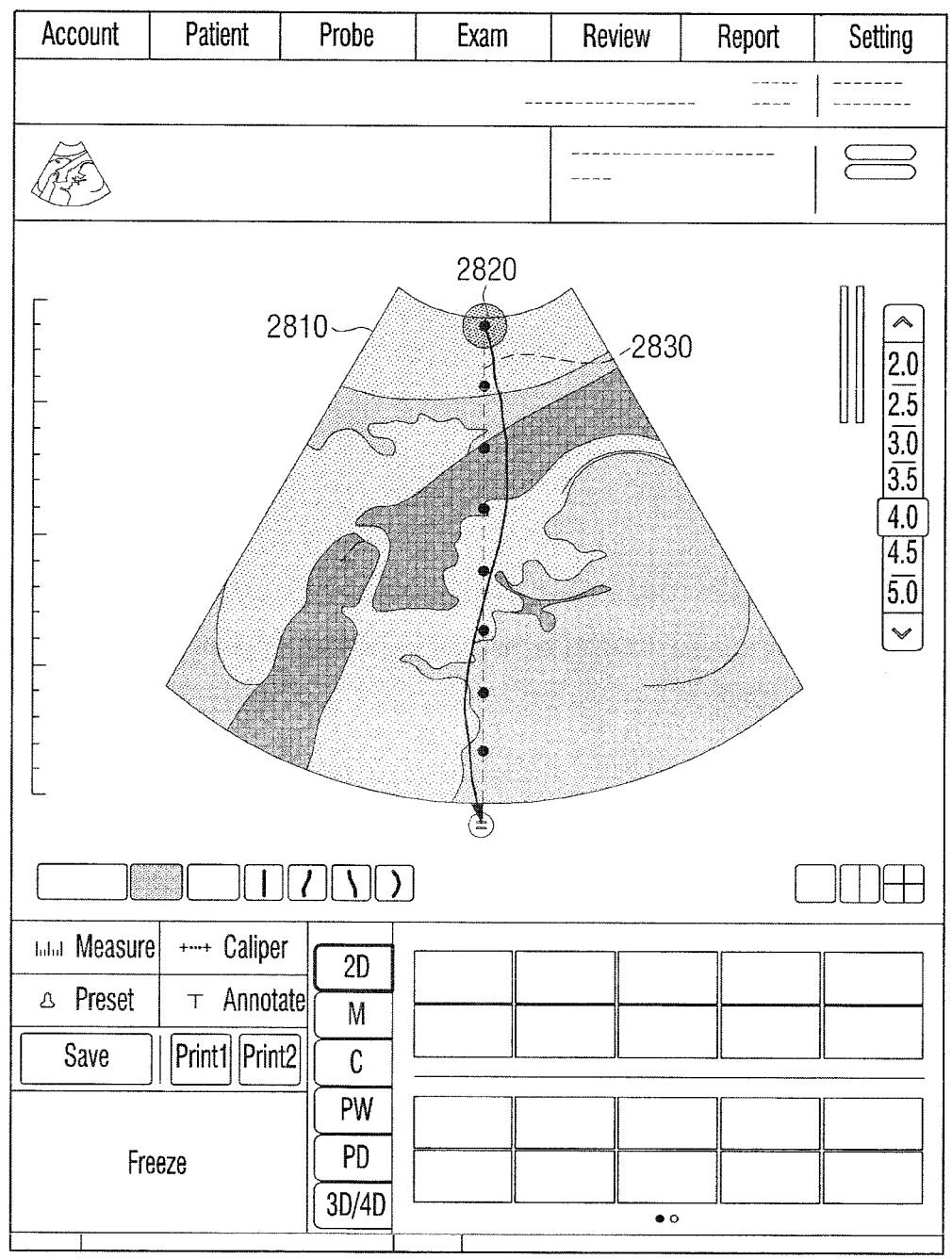
Figure 28C:
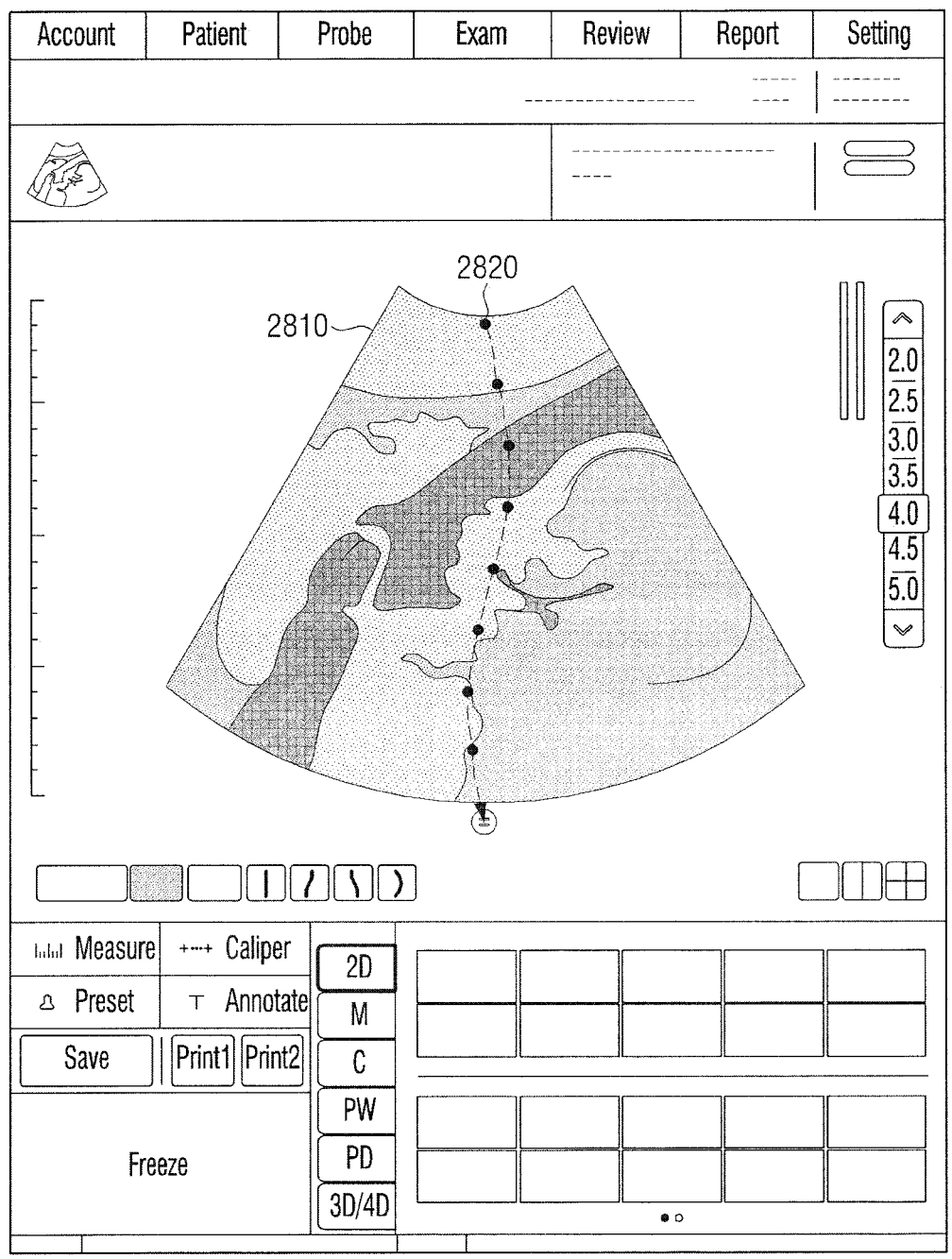

FIGS. 28A, 28B, and 28C illustrate a manipulation of setting a TGC according to an embodiment of the present disclosure.

Referring to FIG. 28A, the user may touch a TGC button 2820 of a screen 2800 for setting a TGC.

Referring to FIG. 28B, a TGC line 2820 is displayed over the ultrasound image 2810. The TGC line 2820 may be associated with a default configuration or may be a line previously defined by a user. The TGC line 2820 includes a segment 2830 in order to visualize a plurality of manipulating points for adjusting a gain of a reflected wave being received in each of the plurality of depth regions divided from an ultrasound image. In an exemplary embodiment, a size of a gain corresponding to a depth region where a manipulating point belongs is determined based on how much the manipulating point is distanced from a central axis, that is, a criteria.

The user may perform a manipulation of sweeping according to a position at each depth region corresponding to a desired gain from a top end of the ultrasound image to a depth direction.

Referring to FIG. 28C, a state where a TGC line 2820 is displayed to indicate the manipulating points of each depth region that have moved to points where a user's touch has been detected such that the user may set the TGC by only one touch manipulation is illustrated.

FIGS. 29A to 29D are views illustrating a manipulation of changing a TGC setting according to an embodiment of the present disclosure.

Figure 29A:
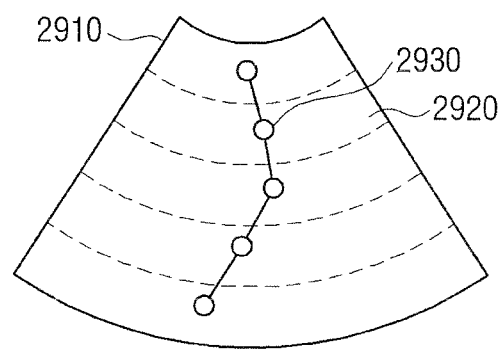
FIGS. 29A to 29D are views illustrating a manipulation of changing a TGC setting according to an embodiment of the present disclosure.

Referring to FIG. 29A, an ultrasound image 2910 has been divided into five depth regions 2920. In addition, five manipulating points 2930 are arranged, where one manipulating point is associated with each depth region 2920 and a TGC line connected the manipulating points 2930 are displayed.

Figure 29B:
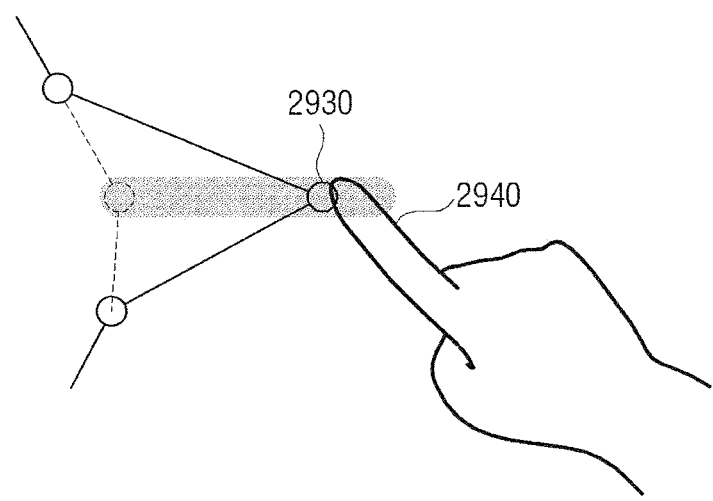

Referring to FIG. 29B, the user may set the TGC by directly touching and dragging 2940 one or more of the manipulating points 2930.

Figure 29C:
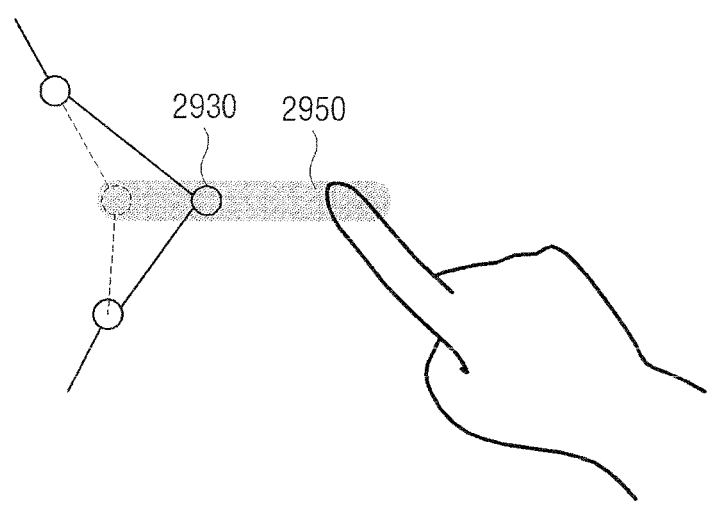

Referring to FIG. 29C, the user may move the manipulating points 2930 in predetermined units by the manipulation 2950 of touching and dragging the manipulating point within the depth region 2920 associated with the manipulating point 2930. In an exemplary embodiment, the user may move the manipulating points 2930 in smaller units than the movement distances of the touched points by the dragging through the manipulation 2950 of touching and dragging the periphery of the manipulating points 2930.

Figure 29D:
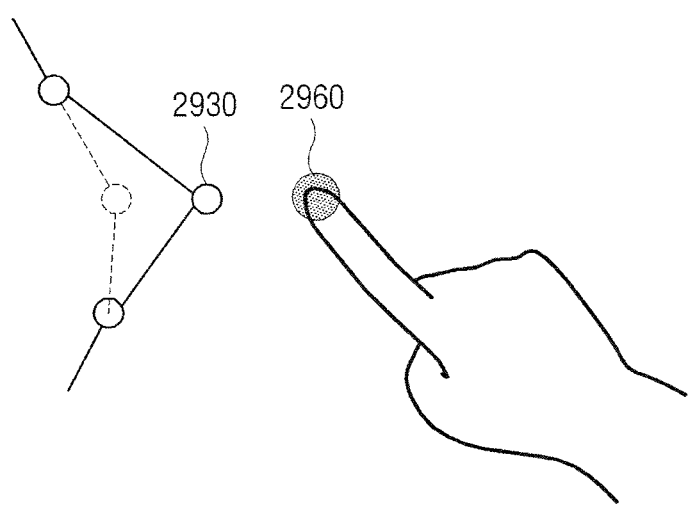

Referring to FIG. 29D, the user may move the manipulating points 2930 in predetermined units through a manipulation 2960 of tapping the periphery of the manipulating points 2930 in the depth region 2920 associated with the manipulating point 2930. For example, a direction of movement of the manipulating points may be determined by whether a position of the tapping is left or right of the manipulating points.

The aforementioned TGC setting method is capable of fine controlling a gain with only touch manipulations.

Touch Interaction for Marking

Figure 30:
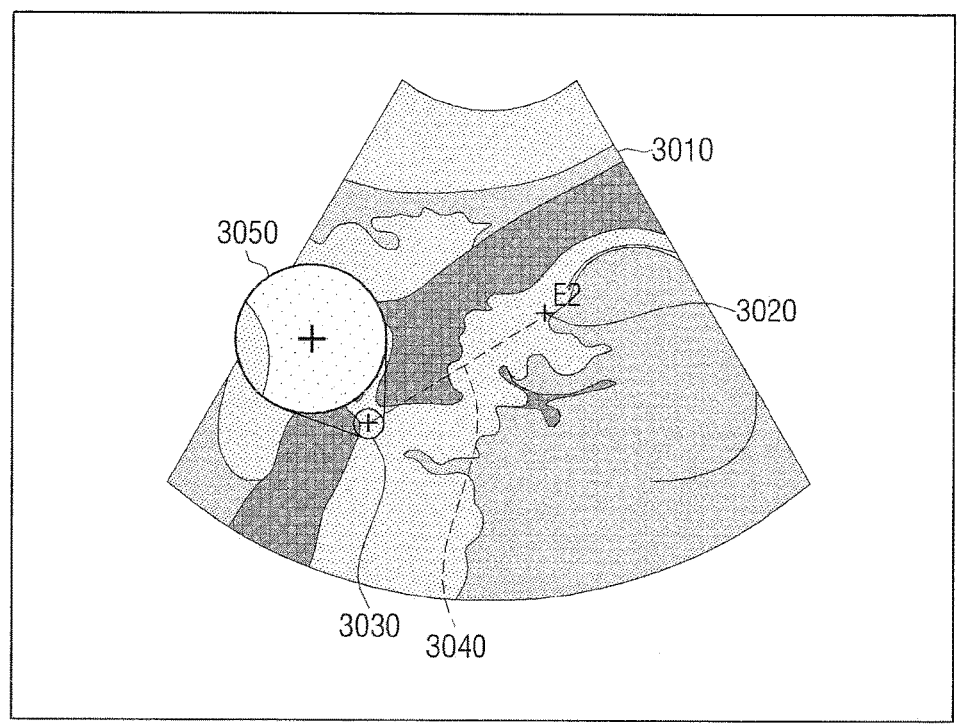
FIG. 30 is a view illustrating a measuring function according to an embodiment of the present disclosure.

FIG. 30 is a view illustrating a measuring function according to an embodiment of the present disclosure.

Referring to FIG. 30, an ultrasound image 3010 is displayed on an image region, and over the ultrasound image 3010, two points 3020, 3030 are displayed by execution of a caliper function. In addition, a segment 3040 is displayed connecting the two points. In an exemplary embodiment, an expanded image 3050 of the periphery of the point 3030 is displayed on the image region thereby enabling the user to identify the exact position of the marker displayed.

Figure 31A:
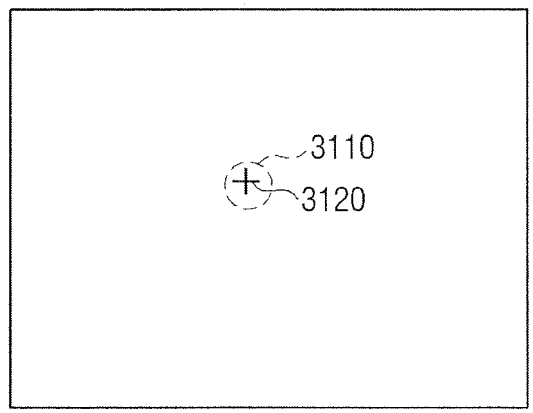
FIGS. 31A and 31B are views illustrating a manipulation of displaying a mark on an ultrasound image according to an embodiment of the present disclosure.
Figure 31B:
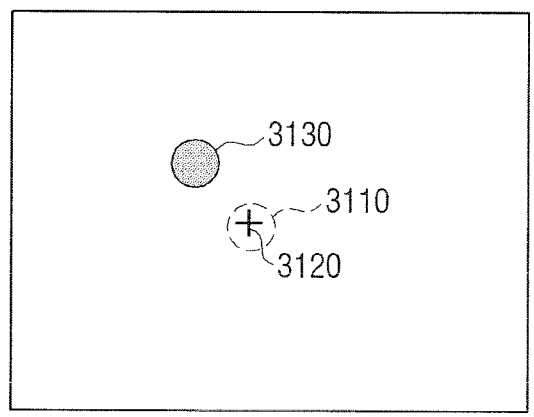

FIGS. 31A to 31B illustrate a manipulation of displaying a mark on an ultrasound image according to an embodiment of the present disclosure.

Referring to FIG. 31A, a mark 3120 is displayed on a point 3110 where a touch has been detected in a still ultrasound image. In an exemplary embodiment, the point 3110 where the touch has been detected may be more than one point or a spatial area. In an exemplary embodiment, the position where the mark 3120 is displayed may be the very center of the point 3110 where the touch has been detected.

The user may change the position where the mark is to be displayed by moving the touched point 3110 on the touch display 110. As the user releases the initial touch without further manipulation and if no further touch is detected, the mark 3120 will not be further displayed either.

Referring to FIG. 31B, when a touch 3130 is detected at another point while the initial touch 3110 on a still ultrasound image is maintained, the position of the mark 3120 displayed is fixed. More specifically, when a second touch 3130 is detected after the initial touch 3110, it is possible to display the mark 3120 displayed by the initial touch 3110 fixatedly on the screen regardless of the movement or release of the touch 3110.

The aforementioned touch interaction of displaying a mark is capable of displaying a mark precisely without occurrences of dislocating the mark by faltering in releasing the touch.

Figure 32A:
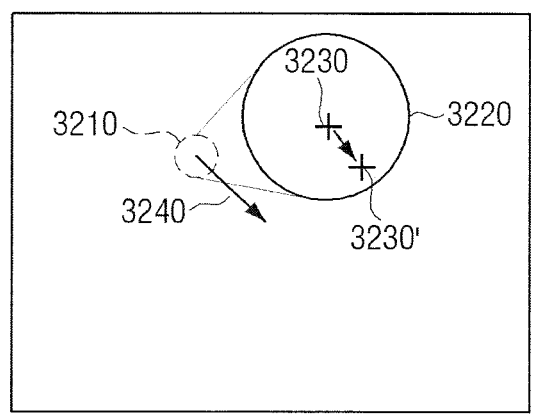
FIGS. 32A and 32B are views illustrating a manipulation of displaying a mark on an ultrasound image according to an embodiment of the present disclosure.
Figure 32B:
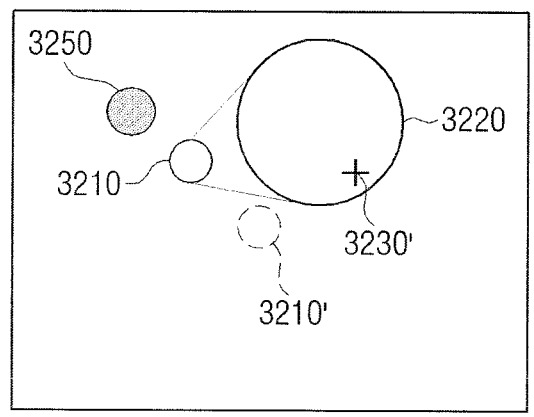

FIGS. 32A and 32B are views illustrating a manipulation of displaying a mark on an ultrasound image according to another embodiment of the present disclosure.

Referring to FIG. 32A, a touch 3210 for displaying a mark on a still ultrasound image is detected. Then, an expanded image 3220 of the periphery of the point where the touch 3210 has been detected is displayed fixatedly.

A mark 3230 is displayed on the expanded image 3220. More specifically, on the expanded image 3220, the mark 3230 may be displayed on a position in the expanded image corresponding to a position in a general image where the mark is to be displayed by the touch 3210.

The user may perform a manipulation 3240 by dragging the point where the initial touch has been made. In addition, when the touch is dragged, the mark 3230 is moved within the expanded image to marker 3230'. In an exemplary embodiment, a direction of movement of the mark 3230 may correspond to the direction of the detected dragging manipulation, but the distance of movement of the mark 3230 may be smaller than the distance of movement of the touched point made by the dragging manipulation. In addition, the range in which the mark 3230 may be moved by the dragging manipulation may be restricted to within the expanded image.

Referring to FIG. 32B, when the dragged touch point 3210' is retained, a marker 3230' is displayed on the expanded region 3220. In addition, when a touch 3250 is detected from another point, the marker 3230' is displayed fixately. More specifically, the user may confirm a point to display a mark 3230 within the expanded region 3230 through a dragging manipulation 3240 of a first touch 321, and then when a mark 3230' is moved, a second touch 3250 is performed, thereby fixating the displaying of the mark 3230'.

The aforementioned touch interaction of displaying a mark is capable of adjusting a position to display the mark precisely with only touch manipulations.

Meanwhile, even if it is explained in the present specification that all the components of the embodiments of the present disclosure are combined to one another or operate in combinations to one another, there is no limitation thereto. That is, as long as it is within the purpose of the present disclosure, one or more of the components may be selectively combined. In addition, one or more of the components may be selectively combined and embodied as a computer program having a program module that performs one or more functions combined in one or more hardware. Codes and code segments that configure such a computer program may be easily conceived by one skilled in the related art. Such a computer program may be stored in a non-transitory computer readable medium, and then be read and executed by the computer, thereby providing the embodiments of the present disclosure.

In an exemplary embodiment, a non-transitory computer readable medium refers to a computer readable medium that is configured to store data semi-permanently unlike a medium that stores data for a short period of time such as a register, cache, and memory and the like. More specifically, the aforementioned programs may be stored in and provided through a non-transitory computer readable medium such as a CD, DVD, hard disk, blue ray disk, USB, memory card, and ROM and the like.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An ultrasound diagnosis apparatus for emitting ultrasound waves to an examination object and obtaining an ultrasound image, the apparatus comprising:
   a touch display; and
   a controller configured to:
   control the touch display to display the ultrasound image, and
   in response to receiving a touch input to the ultrasound image displayed on the touch display, set a focus or a depth of the ultrasound image based on a touched position of the touch input,
   wherein the ultrasound image comprises a plurality of depth areas that are obtained by focusing focal points on a plurality of depths of the ultrasound image, and
   wherein the controller is further configured to:
   control display of a plurality of manipulating points corresponding to the plurality of depth areas, and
   based on a second touch input for selecting a manipulating point from among the plurality of manipulating points, change a total gain compensation (TGC) of a depth area, from among the plurality of depth areas, corresponding to the selected manipulating point.

2. The apparatus according to claim 1, wherein the controller is further configured to set a focus region at a depth corresponding to the touched position to be in focus so as to change a resolution of the ultrasound image, when the touch input associated with the ultrasound image is received.

3. The apparatus according to claim 1, wherein the controller is further configured to:
   in response to the receiving of the touch input at a first corner from among two corner regions parallel to a depth direction of the ultrasound image, set the focus of the ultrasound image corresponding to the touched position at the first corner, and
   in response to the receiving of the touch input at a second corner, set the depth of the ultrasound image corresponding to the touched position at the second corner.

4. The apparatus according to claim 1, wherein the controller is further configured to, in response to the receiving of the touch input of dragging a corner region at an end of a depth direction of the ultrasound image which is displayed, set the depth of the ultrasound according to a position associated with a location in which a first corner region or a second corner region is dragged.

5. The apparatus according to claim 1, wherein the controller is further configured to:
   control display of the plurality of manipulating points on each of the plurality of depth areas that configure the ultrasound image, and
   in response to the receiving of the second touch input within the depth area corresponding to the selected manipulating point, move one of the plurality of manipulating points according to predetermined units, and change the TGC according to a distance and a direction by which the one of the plurality of manipulating points is moved.

6. The apparatus according to claim 5, wherein the controller is further configured to, in response to the receiving of the touch input of dragging within the depth area, move the one of the plurality of manipulating points within the depth area where the touch input of dragging is detected according to smaller units than the distance by which the one of the plurality of manipulating points is moved by the touch input of dragging.

7. The apparatus according to claim 5, wherein the controller is further configured to, in response to the receiving of the touch input of tapping within the depth area, move the one of the plurality of manipulating points within the depth area where the tapping is detected according to the predetermined units based on a number of times the touch input of tapping is received.

8. The apparatus according to claim 1, wherein the controller, in response to a predetermined event occurring, is further configured to:
   control the touch display to display a still image of the ultrasound image,
   control the touch display to display a mark on a point where a touch is detected in the still image of the ultrasound image, and
   in response to detecting a touch in another point with the touch of the still image of the ultrasound image being retained, fixate a position of the displayed mark.

9. The apparatus according to claim 8, wherein the controller is further configured to:

control the touch display to display an expanded image of a periphery associated with the point where the touch is detected in the still image of the ultrasound image, control the touch display to display a mark on the expanded image, wherein the displayed mark on the expanded image corresponds to the point where the touch is detected in the still image of the ultrasound image, and in response to the touch on the still image of the ultrasound image being dragged, move the mark within the expanded image.

10. The apparatus according to claim 9, wherein the controller is further configured to move the mark within the expanded image according to smaller units than a distance which the touch on the still image of the ultrasound image is moved by being dragged.

11. A method of controlling an ultrasound diagnosis apparatus for emitting ultrasound waves to an examination object and obtaining an ultrasound image, the method comprising:

displaying a screen that includes the ultrasound image;

receiving a touch input associated with the ultrasound image; and in response to receiving the touch input, setting a focus or a depth of the ultrasound image based on a touched position of the touch input, wherein the ultrasound image comprises a plurality of depth areas that are obtained by focusing focal points on a plurality of depths of the ultrasound image, and wherein the method further comprises:

displaying a plurality of manipulating points corresponding to the plurality of depth areas, and based on a second touch input for selecting a manipulating point from among the plurality of manipulating points, changing a total gain compensation (TGC) of a depth area, from among the plurality of depth areas, corresponding to the selected manipulating point.

12. The method according to claim 11, wherein the setting of the focus, in response to the receiving of the touch input associated with the ultrasound image, sets a focus region at a depth corresponding to the touched position to be in focus so as to change a resolution of the ultrasound image.

13. The method according to claim 11, wherein the setting of the focus, in response to the receiving of the touch input at a first corner from among two corner regions parallel to a depth direction of the ultrasound image, sets the focus of the ultrasound image corresponding to the touched position at the first corner, and wherein the setting of the focus, in response to the receiving of the touch input at a second corner, sets the depth of the ultrasound image corresponding to the touched position at the second corner.

14. The method according to claim 11, wherein the setting of the focus, in response to the receiving of the touch input of dragging a corner region at an end of a depth direction of the ultrasound image which is displayed, sets the depth of the ultrasound image according to a position in which the corner region is dragged.

15. The method according to claim 11, wherein the setting of the focus further comprises displaying the plurality of manipulating points on each of the plurality of depth areas associated with the ultrasound image, and wherein the method further comprises:

in response to the receiving of the second touch input within the depth area corresponding to the selected manipulating point, moving the one of the plurality of manipulating points according to predetermined units, and changing the TGC based on a distance and a direction by which the one of the plurality of manipulating points is moved.

16. The method according to claim 15, wherein the moving of the one of the plurality of manipulating points, in response to the receiving of the touch input of dragging within the depth areas, moves the one of the plurality of manipulating points within the depth areas where the dragging is detected according to smaller units than the distance by which the one of the plurality of manipulating points is moved by the touch input of dragging.

17. The method according to claim 15, wherein the moving of the one of the plurality of manipulating points, in response to receiving a touch input of tapping within the depth areas, moves the one of the plurality of manipulating points within the depth areas where the tapping is detected according to the predetermined units according to a number of times the touch input of tapping is received.

18. The method according to claim 11, further comprising:

in response to a predetermined event occurring, displaying a still image of the ultrasound image;

displaying a mark on a first point where a touch is detected in the still image of the ultrasound image; and in response to detecting a touch at a second point with the touch associated with the first point being retained, fixating a position of the displayed mark.

19. The method according to claim 11, further comprising:

displaying an expanded image of a periphery of a point where the touch input is detected in the still image of the ultrasound image;

displaying a mark on the expanded image, wherein the mark is associated with the point where the touch input is detected in the still image of the ultrasound image; and in response to the touch input being detected on the still image of the ultrasound image being dragged, moving the displayed mark within the expanded image.

20. The method according to claim 19, wherein the moving of the mark within the expanded image includes moving the mark within the expanded image according to smaller units than a distance by which the touch input on the still image of the ultrasound image is moved by being dragged.

* * * * *